(12) United States Patent
Akahata et al.

(10) Patent No.: US 12,227,770 B2
(45) Date of Patent: Feb. 18, 2025

(54) ALPHAVIRUS REPLICON PARTICLE

(71) Applicant: VLP Therapeutics, Inc., Wilmington, DE (US)

(72) Inventors: Wataru Akahata, Kensington, MD (US); Ryuji Ueno, Easton, MD (US)

(73) Assignee: VLP Therapeutics, Inc., Wilmington, DE (US)

( * ) Notice: Subject to any disclaimer, the term of this patent is extended or adjusted under 35 U.S.C. 154(b) by 542 days.

(21) Appl. No.: 17/481,495

(22) Filed: Sep. 22, 2021

(65) Prior Publication Data

US 2022/0002682 A1    Jan. 6, 2022

Related U.S. Application Data

(63) Continuation of application No. 16/225,181, filed on Dec. 19, 2018, now abandoned.

(60) Provisional application No. 62/608,213, filed on Dec. 20, 2017.

(51) Int. Cl.
| | |
|---|---|
| *C12N 7/00* | (2006.01) |
| *A61K 39/00* | (2006.01) |
| *A61K 39/12* | (2006.01) |
| *A61K 48/00* | (2006.01) |
| *A61P 35/00* | (2006.01) |
| *C07K 14/005* | (2006.01) |

(Continued)

(52) U.S. Cl.
CPC ........ *C12N 7/00* (2013.01); *A61K 39/001162* (2018.08); *A61K 39/12* (2013.01); *A61P 35/00* (2018.01); *C07K 14/005* (2013.01); *C07K 16/2818* (2013.01); *C12N 15/86* (2013.01); *A61K 48/00* (2013.01); *C12N 2770/36122* (2013.01); *C12N 2770/36123* (2013.01); *C12N 2770/36134* (2013.01); *C12N 2770/36143* (2013.01); *C12N 2770/36152* (2013.01)

(58) Field of Classification Search
None
See application file for complete search history.

(56) References Cited

U.S. PATENT DOCUMENTS

| | | | |
|---|---|---|---|
| 5,185,440 | A | 2/1993 | Davis et al. |
| 5,439,809 | A | 8/1995 | Haynes et al. |
| 5,505,947 | A | 4/1996 | Johnston et al. |

(Continued)

FOREIGN PATENT DOCUMENTS

| | | |
|---|---|---|
| CN | 102321639 A | 1/2012 |
| CN | 106085974 A | 11/2016 |

(Continued)

OTHER PUBLICATIONS

Wataru Akahata et al., "A VLP vaccine for epidemic Chikungunya virus protects non-human primates against infection," Nat. Med., 2010, 16(3); 334-338. (pp. 1-12).

(Continued)

*Primary Examiner* — Michelle S Horning
(74) *Attorney, Agent, or Firm* — Sughrue Mion, PLLC

(57) ABSTRACT

Provided is an alphavirus replicon particle (ARP), which comprises (i) alphavirus structural proteins comprising capsid and/or envelope, and (ii) an alphavirus replicon comprising a polynucleotide encoding alphavirus non-structural proteins nsp1, nsp2, nsp3 and nap4 and at least one gene of interest wherein at least one of capsid, and E3 and E2 in the envelope comprise one or more amino acid alteration but E1 in the envelope comprises no amino acid alteration.

14 Claims, 14 Drawing Sheets

Specification includes a Sequence Listing.

(51) Int. Cl.
*C07K 16/28* (2006.01)
*C12N 15/86* (2006.01)

(56) References Cited

U.S. PATENT DOCUMENTS

| | | | |
|---|---|---|---|
| 5,580,773 | A | 12/1996 | Kang et al. |
| 5,629,204 | A | 5/1997 | Honjo et al. |
| 5,639,650 | A | 6/1997 | Johnston et al. |
| 5,643,576 | A | 7/1997 | Johnston et al. |
| 5,698,520 | A | 12/1997 | Honjo et al. |
| 5,792,462 | A | 8/1998 | Johnston et al. |
| 5,811,407 | A | 9/1998 | Johnston et al. |
| 5,939,598 | A | 8/1999 | Kucherlapati et al. |
| 6,008,035 | A | 12/1999 | Johnston et al. |
| 6,156,558 | A | 12/2000 | Johnston et al. |
| 6,521,235 | B2 | 2/2003 | Johnston et al. |
| 6,531,135 | B1 | 3/2003 | Johnston et al. |
| 6,541,010 | B1 | 4/2003 | Johnston et al. |
| 6,583,121 | B1 | 6/2003 | Johnston et al. |
| 6,783,939 | B2 | 8/2004 | Olmsted |
| 6,844,188 | B1 | 1/2005 | MacDonald et al. |
| 6,982,087 | B2 | 1/2006 | Johnston et al. |
| 7,045,335 | B2 | 5/2006 | Smith et al. |
| 7,078,218 | B2 | 7/2006 | Smith et al. |
| 7,101,550 | B2 | 9/2006 | Wood et al. |
| 7,235,235 | B2 | 6/2007 | Johnston et al. |
| 7,419,674 | B2 | 9/2008 | Chulay et al. |
| 7,425,337 | B2 | 9/2008 | Smith et al. |
| 7,442,381 | B2 | 10/2008 | Smith et al. |
| 7,531,180 | B2 | 5/2009 | Polo et al. |
| 7,572,453 | B2 | 8/2009 | Polo et al. |
| 7,595,048 | B2 | 9/2009 | Honjo et al. |
| 7,790,181 | B2 | 9/2010 | Platteborze et al. |
| 8,158,418 | B2 | 4/2012 | Polo et al. |
| 8,263,092 | B1 | 9/2012 | Smith et al. |
| 8,460,913 | B2 | 6/2013 | Kamrud et al. |
| 8,617,533 | B2 | 12/2013 | Smith et al. |
| 8,680,258 | B2 | 3/2014 | Coffield et al. |
| 8,709,441 | B2 | 4/2014 | Rayner et al. |
| 9,079,943 | B2 | 7/2015 | Rayner et al. |
| 9,187,729 | B2 | 11/2015 | Depaz et al. |
| 9,249,191 | B2 | 2/2016 | Ueno et al. |
| 9,255,126 | B2 | 2/2016 | Polo et al. |
| 9,353,353 | B2 | 5/2016 | Nabel et al. |
| 9,363,353 | B1 | 6/2016 | Chik |
| 9,416,370 | B2 | 8/2016 | Smith et al. |
| 9,441,247 | B2 | 9/2016 | Rayner et al. |
| 9,487,563 | B2 | 11/2016 | Nabel et al. |
| 9,512,190 | B2 | 12/2016 | Ueno et al. |
| 9,597,414 | B2 | 3/2017 | Coffield, III et al. |
| 9,637,532 | B2 | 5/2017 | Akahata et al. |
| 9,969,986 | B2 | 5/2018 | Akahata et al. |
| 10,098,943 | B2 | 10/2018 | Akahata et al. |
| 10,111,943 | B2 | 10/2018 | Smith et al. |
| 10,434,187 | B2 | 10/2019 | Coffield, III et al. |
| 2003/0108521 | A1 | 6/2003 | Calatrava |
| 2003/0232324 | A1 | 12/2003 | Polo et al. |
| 2005/0214321 | A1 | 9/2005 | Rasochova et al. |
| 2007/0122378 | A1 | 5/2007 | Freeman et al. |
| 2008/0025067 | A1 | 1/2008 | Scheuerlein |
| 2008/0118956 | A1 | 5/2008 | Pages |
| 2009/0079185 | A1 | 3/2009 | Carbines-Evans et al. |
| 2009/0298955 | A1 | 12/2009 | Handa et al. |
| 2009/0305950 | A1 | 12/2009 | Minato et al. |
| 2009/0312190 | A1 | 12/2009 | Chinea Santiago et al. |
| 2011/0027306 | A1 | 2/2011 | Rayner et al. |
| 2011/0035004 | A1 | 2/2011 | Maxwell |
| 2011/0081341 | A1 | 4/2011 | Honjo et al. |
| 2011/0171249 | A1 | 7/2011 | Frolov et al. |
| 2011/0207223 | A1 | 8/2011 | Tang et al. |
| 2011/0262389 | A1 | 10/2011 | Mosco |
| 2011/0318373 | A1 | 12/2011 | Sasikumar et al. |
| 2012/0003266 | A1 | 1/2012 | Nabel et al. |
| 2013/0052225 | A1 | 2/2013 | Pushko et al. |
| 2013/0122262 | A1 | 5/2013 | Nagakura et al. |
| 2013/0251744 | A1 | 9/2013 | Ueno et al. |
| 2014/0120125 | A1 | 5/2014 | Ella et al. |
| 2014/0127247 | A1 | 5/2014 | Dubensky, Jr. et al. |
| 2014/0170186 | A1 | 6/2014 | Nabel et al. |
| 2014/0363458 | A1 | 12/2014 | Ueno et al. |
| 2015/0017194 | A1 | 1/2015 | Akahata et al. |
| 2016/0040134 | A1 | 2/2016 | Akahata et al. |
| 2016/0074501 | A1 | 3/2016 | Akahata et al. |
| 2016/0090403 | A1 | 3/2016 | Ueno et al. |
| 2016/0200775 | A1 | 7/2016 | Akahata et al. |
| 2016/0303221 | A1 | 10/2016 | Nabel et al. |
| 2017/0035871 | A1 | 2/2017 | Ueno et al. |
| 2017/0065703 | A1 | 3/2017 | Akahata et al. |
| 2017/0233450 | A1 | 8/2017 | Akahata et al. |
| 2017/0252425 | A1 | 9/2017 | Akahata et al. |

FOREIGN PATENT DOCUMENTS

| | | |
|---|---|---|
| JP | 4-506301 A | 11/1992 |
| JP | 2007-512842 A | 5/2007 |
| JP | 2007-537761 A | 12/2007 |
| JP | 2008-543774 A | 12/2008 |
| RU | 2 398 875 C2 | 9/2010 |
| WO | 93/10152 A1 | 5/1993 |
| WO | 96/37616 A1 | 11/1996 |
| WO | 97/12048 A1 | 4/1997 |
| WO | 99/18226 A2 | 4/1999 |
| WO | 99/41383 A1 | 8/1999 |
| WO | 02/096939 A2 | 12/2002 |
| WO | 03/102166 A2 | 12/2003 |
| WO | 2004/043399 A2 | 5/2004 |
| WO | 2004/085660 A2 | 10/2004 |
| WO | 2006/040334 A1 | 4/2006 |
| WO | 2006/088229 A1 | 8/2006 |
| WO | 2007/003384 A1 | 1/2007 |
| WO | 2007/059715 A2 | 5/2007 |
| WO | 2007/100098 A1 | 9/2007 |
| WO | 2008/025067 A1 | 3/2008 |
| WO | 2009/079185 A2 | 6/2009 |
| WO | 2010/062396 A2 | 6/2010 |
| WO | 2011/035004 A1 | 3/2011 |
| WO | 2012/006180 A1 | 1/2012 |
| WO | 2012/023995 A1 | 2/2012 |
| WO | 2012/106356 A2 | 8/2012 |
| WO | 2012/123755 A1 | 9/2012 |
| WO | 2012/172574 A1 | 12/2012 |
| WO | 2013/009884 A1 | 1/2013 |
| WO | 2013/063248 A1 | 5/2013 |
| WO | 2013/122262 A1 | 8/2013 |
| WO | 2013/151764 A1 | 10/2013 |
| WO | 2015/005500 A1 | 1/2015 |
| WO | 2015/139784 A1 | 9/2015 |
| WO | 2016/021209 A1 | 2/2016 |
| WO | 2016/109792 A2 | 7/2016 |
| WO | 2016/199936 A1 | 12/2016 |
| WO | 2016/210127 A1 | 12/2016 |
| WO | 2017/009873 A1 | 1/2017 |
| WO | 2017/015463 A2 | 1/2017 |

OTHER PUBLICATIONS

Ira Mellman et al., "Cancer immunotherapy comes of age," Nature, 2011, vol. 480 (pp. 480-489).

António Roldão et al., "Virus-like particles in vaccine development", Expert Rev. Vaccines, 2010, 9(10):, pp. 1149-1176.

Gunther Spohn et al., "A Virus-Like Particle-Based Vaccine Selectively Targeting Soluble TNF-α Protects from Arthritis without Inducing Reactivation of Latent Tuberculosis", The Journal of Immunology, 2007, 178: pp. 7450-7457.

Elizabeth V.L. Grgacic et al., "Virus-like particles: Passport to immune recognition", Methods, 2006, 40: pp. 60-65.

Gary T. Jennings et al., "Immunodrugs: Therapeutic VLP-Based Vaccines for Chronic Diseases", Annu. Rev. Pharmacol. Toxicol., 2009, 49: pp. 303-326.

Heinz Leibl et al., "Adjuvant/carrier activity of inactivated tick-borne encephalitis virus", Vaccine, 1998, 16(4): pp. 340-345.

(56) References Cited

OTHER PUBLICATIONS

Bryce Chackerian et al., "Determinants of Autoantibody Induction by Conjugated Papillomavirus Virus-Like Particles", The Journal of Immunology, 2002, 169: pp. 6120-6126.
Maria Lia Palomba et al., "CD8+ T-Cell-Dependent Immunity Following Xenogeneic DNA Immunization against CD20 in a Tumor Challenge Model of B-Cell Lymphoma", Clinical Cancer Research, 2005, 370(11): pp. 370-379.
Wendy K. Roberts et al., "Vaccination with CD20 peptides induces a biologically active, specific immune response in mice", Blood, 2002, 99: pp. 3748-3755.
Kathy D. McCoy et al., "Cytotoxic T Lymphocyte-associated Antigen 4 (CTLA-4) Can Regulate Dendritic Cell-induced Activation and Cytotoxicity of CD8+ T Cells Independently of CD4+ T Cell Help", J. Exp. Med., 1999, 189(7): pp. 1157-1162.
Gregory J. Atkins et al., "Therapeutic and prophylactic applications of alphavirus vectors", Expert Reviews in Molecular Medicine, 2008, 10(e33): pp. 1-17.
Akahata W., and G.J. Nabel, 2012, "A specific domain of the Chikungunya virus E2 protein regulates particle formation in human cells: implications for alphavirus vaccine design," J. Virol. 86(16): pp. 8879-8883.
Kuo, S.-C., et al., 2012, Cell-based analysis of Chikungunya virus E1 protein in membrane fusion, J. Biomed. Sci. 19(44): pp. 1-12.
Siyang Sun et al: "Structural analyses at pseudo atomic resolution of Chikungunya virus and antibodies show mechanisms of neutralization", eLIFE, Apr. 2, 2013, vol. 2, pp. 1-27.
Carvalho et al., "Malaria Vaccine: Candidate Antigens, Mechanisms, Constraints and Prospects," Scand. J. Immunol., Blackwell Science Ltd. Jul. 1, 2002, vol. 56, pp. 327-343.
Crompton et al., "Advances and Challenges in malaria vaccine development," Science in medicine, The Journal of Clinical Investigation, Dec. 2010, vol. 120, No. 12, pp. 4168-4178.
Malaria Vaccine Program, http://www.globalvaccines.org/content/malaria+vaccine+program/19614, 4 pages total (2012).
Rodriguez D et al., Vaccine Efficacy against malaria by the Combination of Porcine Parvovirus-Like Particles and Vaccinia Virus Vectors Expressing CS of Plasmodium, PLoS One, Apr. 17, 2012, vol. 7, No. 4, e34445. (pp. 1-10).
Oliveira GA et al., Safety and enhanced immunogenicity of a Hepatitis B core particle Plasmodium falciparum Malaria vaccine formulated in adjuvant montanide ISA 720 in a Phase I Trial, Infect. Immun., 2005, vol. 73, No. 6, pp. 3587-3597.
Jones RM et al., A plant-produced Pfs25 VLP Malaria Vaccine Candidate Induces Persistent Transmission Blocking Antibodies against Plasmodium falciparum in immunized mice, PLoS One, Nov. 18, 2013, vol. 8, No. 11, e79538, doi: 10.1371/journal.pone.0079538.
Rodrigues M et al., Influenza and Vaccinia viruses expressing Malaria CD8+T and B Cell epitopes. Comparison of their immunogenicity and capacity to induce protective immunity, J. Immunol., 1994, vol. 153, No. 10, pp. 4636-4648. (15 pages).
Pfeiffer B et al., A virosome-mimotope approach to synthetic vaccine design and optimization: synthesis, conformation, and immune recognition of a potential Malaria-vaccine candidate, Angew. Chem. Int. Ed., 2003, vol. 42, No. 21, pp. 2368-2371. (5 pages).
Ghasparian A et al., Engineered synthetic virus-like particles and their use in vaccine delivery, Chembiochem, 2011, vol. 12, No. 1, pp. 100-109.
Dobano C et al., Alphavirus replicon particles are highly immunogenic in the murine Malaria model by homologous or heterologous immunization, Open Vaccine Journal, vol. 1, 2008, pp. 27-37.
Lechner F et al., Virus-like particles as a modular system for novel vaccines, Intervirology, 2002, vol. 45, No. 4-6, pp. 212-217.
Gilbert SC et al., A protein particle vaccine containing multiple Malaria epitopes, Nat. Biotechnol., 1997, vol. 15, No. 12, pp. 1280-1284. (7 pages).
Allsopp CE et al., "Comparison of numerous delivery systems for the induction of cytotoxic T lymphocytes by immunization," Eur. J. Immunol., 1996, vol. 26, No. 8, pp. 1951-1959.
Oliveira-Ferreira et al., "Immunogenicity of Ty-VLP bearing a CD8(+) T cell epitope of the CS protein of P. yoelii: enhanced memory response by boosting with recombinant vaccinia virus.", Vaccine. Mar. 6, 2000; 18(17); 1863-1869.
GenBank: AAW78190.1. circumsporozoite protein, partial [Plasmodium falciparum]. Dec. 29, 2006. (2 pages).
Gregson et al., "Phase 1 Trial of an Alhydrogel Adjuvanted Hepatitis B Core Virus-Like Particle Containing Epitopes of Plasmodium falciparum Circumsporozoite Protein.", PLoS ONE. Feb. 2008 | vol. 3 | Issue 2| e1556.
Adams et al., "The expression of hybrid HIV: Ty virus-like particles in yeast," Nature Sep. 3-9, 1987; 329(6134); pp. 68-70. (9 pages).
Federico M., "Virus-like particles show promise as candidates for new vaccine strategies," Future Virol. (2010) 5(4); pp. 371-374.
Birkett A et al. "A Modified Hepatitis B Virus Core Particle Containing Multiple Epitopes of the Plasmodium falciparum Circumsporozoite Protein Provides a Highly Immunogenic Malaria Vaccine in Preclinical Analyses in Rodent and Primate Hosts", Infection and Immunity, American Society for Microbiology, US, vol. 70, No. 12; Dec. 1, 2002, pp. 6860-6870.
Milich D R et al. "Conversion of poorly immunogenic malaria repeat sequences into a highly immunogenic vaccine candidate", Vaccine, Elsevier Ltd, GB; vol. 20, No. 5-6; Dec. 12, 2001; pp. 771-788.
Shiratsuchi T et al. "Replacing adenoviral vector HVR1 with a malaria B cell epitope improves immunogenicity and circumvents preexisting immunity to adenovirus in mice", Journal of Clinical Investigation; vol. 120, No. 10; Oct. 2010; pp. 3688-3701.
Y. Agata et al., "Expression of the PD-1 antigen on the surface of stimulated mouse T and B lymphocytes," International Immunology, 1996, vol. 8, No. 5, pp. 765-772.
F. Notka et al., "Accelerated clearance of SHIV in rhesus monkeys by virus-like particle vaccines is dependent on induction of neutralizing antibodies", Vaccine, 2000, vol. 18, No. 3-4, p. 291-301.
U. Arora et al., "Virus-like particles displaying envelope domain III of dengue virus type 2 induce virus-specific antibody response in mice", Vaccine, Jan. 2013, vol. 31, No. 6, p. 873-878.
Rodion Gorchakov et al., "Comparative analysis of the alphavirus-based vectors expressing Rift Valley fever virus glycoproteins," Virology, vol. 366 (2007), pp. 212-225.
Sigrid Elshuber et al., "Cleavage of protein prM is necessary for infection of BHK-21 cells by tick-borne encephalitis virus," Journal of General Virology (2003) vol. 84, pp. 183-191.
Simona Ozden et al., "Inhibition of Chikungunya Virus Infection in Cultured Human Muscle Cells by Furin Inhibitors," Journal of Biological Chemistry, vol. 283, No. 32, Aug. 8, 2008 (10 pages total).
Sigrid Elshuber et al., "Resuscitating Mutations in a Furin Cleavage-Deficient Mutant of the Flavivirus Tick-Borne Encephalitis Virus," Journal of Virology, vol. 79, No. 18, Sep. 2005, pp. 11813-11823.
Hevey et al., "Marburg Virus Vaccines Based upon Alphavirus Replicons Protect Guinea Pigs and Nonhuman Primates", Virology, 251: 28-37 (1998).
Bonaldo et al., "Surface Expression of an Immunodominant Malaria Protein B Cell Epitope by Yellow Fever Virus", J. Mol. Biol., 315(4):873-885 (2002).
Vuola et al., "Differential Immunogenicity of Various Heterologous Prime-Boost Vaccine Regimens Using DNA and Viral Vectors in Healthy Volunteers", J. Immunol., 174(1):449-455 (2005).
Calvo-Calle et al., "A Linear Peptide Containing Minimal T- and B-Cell Epitopes of Plasmodium falciparum Circumsporozoite Protein Elicits Protection against Transgenic Sporozoite Challenge", Infection and Immunity, Dec. 2006. vol. 74, No. 12. p. 6929-6939.
Charoensri et al. "An optimized expression vector for improving the yield of dengue virus-like particles from transfected insect cells" Journal of Virological Methods, vol. 205, 2014 (pp. 116-123).
Cox et al. "Predicting Zika virus structural biology: Challenges and opportunities for intervention" Antiviral Chemistry and Chemotherapy, vol. 24 (3-4), 2015 (pp. 118-126).
De Wispelaere Melissanne, et al., "Mutagenesis of the DI/DIII Linker in Dengue Virus Envelope Protein Impairs Viral Particle Assembly", Journal of Virology, 2012, vol. 86, No. 13, pp. 7072-7083, ISSN: 0022-538X, Abstract, Fig.1, Fig.8-9, p. 7073.

(56) References Cited

OTHER PUBLICATIONS

GenBank: AAB02517.1, "structural polyprotein precursor [Venezuelan equine encephalitis virus]", dated Nov. 17, 2004, retrieved from https://www.ncbi.nlm.nih.gov/protein/AAB02517.1.
GenBank: ADG95942.1, structural polyprotein [Chikungunya virus] http://www.ncbi.nlm.nih.gov/protein/296124572?report=genbank&log$=protalign&blast_rank=2&FiID=PBR7NTOU015. Dec. 28, 2010.
GenBank "Zika virus strain MR 766, complete genome" AY632535.2, Nov. 23, 2010 (6 pages total) [Retrieved on May 16, 2017] Retrieved from the Internet, URL: <https://www.ncbi.nlm.nih.gov/nuccore/AY632535>.
Haddow A. D. et al., "Genetic Characterization of Zika Virus Strains: Geographic Expansion of the Asian Lineage" PLOS Neglected Tropical Disease, Feb. 2012, vol. 6, Issue 2, e1477 (7 pages total).
Vitrop-Duits et al., Human CD4+T cells stimulated by conserved adenovirus 5 hexon peptides recognize cells infected with different species of human adenovirus, Eur. J. Immunol. 2006, vol. 36, pp. 2410-2423.
Metz et al., PLoS ONE, 2011, vol. 6, Issue 10, pp. 1-10.
Liu et al., "Recombinant dengue virus-like particles from Pichia pastoris: efficient production and immunological properties," Vir. Genes, 2010: 40:53-59.
Berthet et al. GenBank: AHF49783.1; 2015.
Enfissi et al. GenBank: ALX35659.1, 2016.
Pushko, et al., Replicon-Helper Systems from Attenuated Venezuelan Encephalitis Virus: Expression of Heterologous Genes in Vitro and Immunization against Heterologous Pathogens in Vivo, Virology 239, 1997 (pp. 389-401).
Manjila, et al., "Novel gene delivery systems", International Journal of Pharmaceutical Investigation, vol. 3, Issue 1, Jan. 2013 (7 pages).
International Search Report and Written Opinion, dated Mar. 26, 2019, issued by the International Searching Authority in PCT/JP2018/046794.
Jose et al. A structural and functional perspective of alphavirus replication and assembly. Future Microbiol. Sep. 2009; 4(7): 837-56. (Year: 2009).
Garmashova et al. Journal of Virology, Analysis of Venezuelan Equine Encephalitis Virus Capsid Protein Function in the Inhibition of Cellular Transcription Dec. 2007, p. 13552-13565. (Year: 2007).
Taylor et al. mBio . Mutation of the N-Terminal Region of Chikungunya Virus Capsid Protein: Implications for Vaccine Design Feb. 21, 2017 ;8(1):e01970-16. (Year: 2017).
Kim et al., "Enhancement of protein expression by alphavirus replicons by designing self-replicating subgenomic RNAs", PNAS, vol. 111. No. 29, Jul. 2014, pp. 10708-10713 (6 pages total).
Extended European Search report, dated Aug. 11, 2021, issued by the European Patent Office in EP Application No. 18892003.7.
Eryu WANG et al., "Chimeric Alphavirus vaccine candidates for chikungunya", Vaccine, vol. 26, 2008, pp. 5030-5039 (10 pages).
Hsieh Szu-Chia, et al., "A strong endoplasmic reticulum retention signal in the stem-anchor region of envelope glycoprotein of dengue virus type 2 affects the production of virus-like particles", Virology, 2008, vol. 374, No. 2, pp. 338-350, ISSN: 0042-6822.
Hsieh Szu-Chia et al. "The length of and nonhydrophobic residues in the transmembrane domain of dengue virus envelope protein are critical for its retention and assembly in the endoplasmic reticulum" Journal of Virology, vol. 84 No. 9, Apr. 2010 (pp. 4782-4797).

WHO Dengue vaccine research, "Immunization, Vaccines and Biologicals", http://www.who.int/immunization/research/development/dengue_vaccines/en/ (total 3 pages) 2015.
Huang Claire Y.H., et al., "The dengue virus type 2 envelope protein fusion peptide is essential for membrane fusion", Virology, 2010, vol. 396, No. 2, pp. 305-315, ISSN:0042-6822, Table, Fig.5, pp. 310-313.
Khetarpal Niyati, et al., "Dengue-specific subviral nanoparticles: design, creation and characterization", Journal of Nanobiotechnology, 2013, vol. 11, No. 15, total 8 pages, ISSN: 1477-3155.
Kostyuchenko V et al., "Structure of the thermally stable Zika virus", Nature, May 19, 2016, vol. 533, pp. 425-428.
Larocca et al., "Vaccine Protection Against Zika Virus from Brazil", Nature, Aug. 25, 2016, 536(7617), 474-478, doi:10.1038/nature18952 (24 pages total).
Lin et al., "Analysis of Epitopes on Dengue Virus Envelope Protein Recognized by Monoclonal Antibodies and Polyclonal Human Sera by a High Throughput Assay", PLOS, Jan. 2012, 6(1):e1447, total 12 pages.
Purdy D et al., "Secretion of noninfectious dengue virus-like particles and identification of amino acids in the stem region involved in intracellular retention of envelope protein" Virology, 2005, vol. 333, No. 2, pp. 239-250, ISSN: 0042-6822, Abstract, Fig. 1-4. Table 1, pp. 240, 247-248.
Richner et al. "Modified mRNA vaccines protect against Zika Virus infection" Cell, vol. 168., Mar. 9, 2017 , pp. 1114-1125, (23 pages total).
Seligman S, "Constancy and diversity in the flavivirus fusion peptide", BioMed Central, Virology Journal 2008, Feb. 14, 2008, total 10 pages. URL: http://www.virologyj.com/content/5/1/27.
Taylor et al. "Production of immunogenic West Nile virus-like particles using a herpes simplex virus 1 recombinant vector" Virology, vol. 496, 2016 (pp. 186-193).
Tsai et al., "Complexity of Neutralizing Antibodies against Multiple Dengue Virus Serotypes after Heterotypic Immunization and Secondary Infection Revealed by In-Depth Analysis of Cross-Reactive Antibodies", Journal of Virology, Jul. 2015, vol. 89, No. 14, pp. 7348-7362.
Heinz F et al., "Flaviviruses and flavivirus vaccines", Vaccine 30 (2012) 4301-4306.
Yamaji et al. "Efficient production of Japanese encephalitis virus-like particles by recombinant lepidopteran insect cells" Appl. Microbiol Biotechnol, vol. 97, 2013 (pp. 1071-1079).
Zhang et al., "Vaccination with dengue virus-like particles induces humoral and cellular immune responses in mice", Virology Journal, 2011, 8:333, total 9 pages.
Zika virus fact sheet, updated Sep. 6, 2016; URL:http://www.who.int/mediacentre/factssheets/zika/en/ (5 pages total).
Urakami et al., "Development of a Novel Virus-Like Particle Vaccine Platform That Mimics the Immature Form of Alphavirus," Clinical and Vaccine Immunology, 24(7): e00090-17 (pp. 1-14). 2017.
Veltrop-Duits et al., "Human CD4+ T cells stimulated by conserved adenovirus 5 hexon peptides recognize cells infected with different species of human adenovirus", Eur. J. Immunol., 2006, vol. 36, pp. 2410-2423 (14 pages total).
Akane Urakami et al., "An Envelope-Modified Tetravalent Dengue Virus-Like-Particle Vaccine Has Implications for Flavivirus Vaccine Design", Journal of Virology, Dec. 2017, vol. 91, Issue 23, e01181-17 (16 pages total).
Palucha et al., "Virus-Like Particles: Models for Assembly Studies and Foreign Epitope Carriers," Progress in Nucleic Acid Research and Molecular Biology, 2005, vol. 30, pp. 135-168.

Figure 7

Infectivity Assay

VRPs harvested at 48 or 72 hpt

↓ Infect 293T cells

Dilution: Undiluted, 2-fold, 4-fold, 8-fold, 16-fold serial dilution

↓ 24 hpi

Replace VRPs with fresh DMEM

↓

Measure Luciferase Activity in infected cells 24 or 48 or 72 hpi

SEQUENCE LISTING

<160> NUMBER OF SEQ ID NOS: 12

<210> SEQ ID NO 1
<211> LENGTH: 275
<212> TYPE: PRT
<213> ORGANISM: Venezuelan Equine Encephalitis Virus

<400> SEQUENCE: 1

```
Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Lys
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp
        275
```

<210> SEQ ID NO 2
<211> LENGTH: 275
<212> TYPE: PRT
<213> ORGANISM: Venezuelan Equine Encephalitis Virus

<400> SEQUENCE: 2

```
Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
```

```
            35                  40                  45
Thr Phe Lys Gln Arg Arg Asp Ala Pro Pro Glu Gly Pro Ser Ala Asn
 50                  55                  60

Lys Pro Lys Lys Glu Ala Ser Gln Lys Gln Lys Gly Gly Gln Gly
 65                  70                  75                  80

Lys Lys Lys Lys Asn Gln Gly Lys Lys Ala Lys Thr Gly Pro Pro
                 85                  90                  95

Asn Pro Lys Ala Gln Asn Gly Asn Lys Lys Thr Asn Lys Lys Pro
                100                 105                 110

Gly Lys Arg Gln Arg Met Val Met Lys Leu Glu Ser Asp Lys Thr Phe
                115                 120                 125

Pro Ile Met Leu Glu Gly Lys Ile Asn Gly Tyr Ala Cys Val Val Gly
                130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
                180                 185                 190

His Glu Lys Pro Gln Gly Tyr Tyr Ser Trp His His Gly Ala Val Gln
                195                 200                 205

Tyr Glu Asn Gly Arg Phe Thr Val Pro Lys Gly Val Gly Ala Lys Gly
                210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
                260                 265                 270

Glu Gln Trp
                275

<210> SEQ ID NO 3
<211> LENGTH: 980
<212> TYPE: PRT
<213> ORGANISM: Venezuelan Equine Encephalitis Virus

<400> SEQUENCE: 3

Ser Leu Val Thr Thr Met Cys Leu Leu Ala Asn Val Thr Phe Pro Cys
 1                   5                  10                  15

Ala Gln Pro Pro Ile Cys Tyr Asp Arg Lys Pro Ala Glu Thr Leu Ala
                 20                  25                  30

Met Leu Ser Val Asn Val Asp Asn Pro Gly Tyr Asp Glu Leu Leu Glu
                 35                  40                  45

Ala Ala Val Lys Cys Pro Gly Arg Lys Arg Arg Ser Thr Glu Glu Leu
 50                  55                  60

Phe Asn Glu Tyr Lys Leu Thr Arg Pro Tyr Met Ala Arg Cys Ile Arg
 65                  70                  75                  80

Cys Ala Val Gly Ser Cys His Ser Pro Ile Ala Ile Glu Ala Val Lys
                 85                  90                  95

Ser Asp Gly His Asp Gly Tyr Val Arg Leu Gln Thr Ser Ser Gln Tyr
                100                 105                 110

Gly Leu Asp Ser Ser Gly Asn Leu Lys Gly Arg Thr Met Arg Tyr Asp
                115                 120                 125
```

-continued

Met His Gly Thr Ile Lys Glu Ile Pro Leu His Gln Val Ser Leu Tyr
    130                 135                 140

Thr Ser Arg Pro Cys His Ile Val Asp Gly His Gly Tyr Phe Leu Leu
145                 150                 155                 160

Ala Arg Cys Pro Ala Gly Asp Ser Ile Thr Met Glu Phe Lys Lys Asp
                165                 170                 175

Ser Val Arg His Ser Cys Ser Val Pro Tyr Glu Val Lys Phe Asn Pro
            180                 185                 190

Val Gly Arg Glu Leu Tyr Thr His Pro Glu His Gly Val Glu Gln
        195                 200                 205

Ala Cys Gln Val Tyr Ala His Asp Ala Gln Asn Arg Gly Ala Tyr Val
    210                 215                 220

Glu Met His Leu Pro Gly Ser Glu Val Asp Ser Ser Leu Val Ser Leu
225                 230                 235                 240

Ser Gly Ser Ser Val Thr Val Thr Pro Pro Asp Gly Thr Ser Ala Leu
                245                 250                 255

Val Glu Cys Glu Cys Gly Gly Thr Lys Ile Ser Glu Thr Ile Asn Lys
            260                 265                 270

Thr Lys Gln Phe Ser Gln Cys Thr Lys Lys Glu Gln Cys Arg Ala Tyr
        275                 280                 285

Arg Leu Gln Asn Asp Lys Trp Val Tyr Asn Ser Asp Lys Leu Pro Lys
    290                 295                 300

Ala Ala Gly Ala Thr Leu Lys Gly Lys Leu His Val Pro Phe Leu Leu
305                 310                 315                 320

Ala Asp Gly Lys Cys Thr Val Pro Leu Ala Pro Glu Pro Met Ile Thr
                325                 330                 335

Phe Gly Phe Arg Ser Val Ser Leu Lys Leu His Pro Lys Asn Pro Thr
            340                 345                 350

Tyr Leu Ile Thr Arg Gln Leu Ala Asp Glu Pro His Tyr Thr His Glu
        355                 360                 365

Leu Ile Ser Glu Pro Ala Val Arg Asn Phe Thr Val Thr Glu Lys Gly
    370                 375                 380

Trp Glu Phe Val Trp Gly Asn His Pro Pro Lys Arg Phe Trp Ala Gln
385                 390                 395                 400

Glu Thr Ala Pro Gly Asn Pro His Gly Leu Pro His Glu Val Ile Thr
                405                 410                 415

His Tyr Tyr His Arg Tyr Pro Met Ser Thr Ile Leu Gly Leu Ser Ile
            420                 425                 430

Cys Ala Ala Ile Ala Thr Val Ser Val Ala Ala Ser Thr Trp Leu Phe
        435                 440                 445

Cys Arg Ser Arg Val Ala Cys Leu Thr Pro Tyr Arg Leu Thr Pro Asn
450                 455                 460

Ala Arg Ile Pro Phe Cys Leu Ala Val Leu Cys Cys Ala Arg Thr Ala
465                 470                 475                 480

Arg Ala Glu Thr Thr Trp Glu Ser Leu Asp His Leu Trp Asn Asn Asn
                485                 490                 495

Gln Gln Met Phe Trp Ile Gln Leu Leu Ile Pro Leu Ala Ala Leu Ile
            500                 505                 510

Val Val Thr Arg Leu Leu Arg Cys Val Cys Val Val Pro Phe Leu
        515                 520                 525

Val Met Ala Gly Ala Ala Gly Ala Gly Ala Tyr Glu His Ala Thr Thr
530                 535                 540

Met Pro Ser Gln Ala Gly Ile Ser Tyr Asn Thr Ile Val Asn Arg Ala

```
                    545                 550                 555                 560
            Gly Tyr Ala Pro Leu Pro Ile Ser Ile Thr Pro Thr Lys Ile Lys Leu
                                565                 570                 575
            Ile Pro Thr Val Asn Leu Glu Tyr Val Thr Cys His Tyr Lys Thr Gly
                        580                 585                 590
            Met Asp Ser Pro Ala Ile Lys Cys Cys Gly Ser Gln Glu Cys Thr Pro
                    595                 600                 605
            Thr Tyr Arg Pro Asp Glu Gln Cys Lys Val Phe Thr Gly Val Tyr Pro
                    610                 615                 620
            Phe Met Trp Gly Gly Ala Tyr Cys Phe Cys Asp Thr Glu Asn Thr Gln
            625                 630                 635                 640
            Val Ser Lys Ala Tyr Val Met Lys Ser Asp Asp Cys Leu Ala Asp His
                                645                 650                 655
            Ala Glu Ala Tyr Lys Ala His Thr Ala Ser Val Gln Ala Phe Leu Asn
                            660                 665                 670
            Ile Thr Val Gly Glu His Ser Ile Val Thr Val Tyr Val Asn Gly
                        675                 680                 685
            Glu Thr Pro Val Asn Phe Asn Gly Val Lys Ile Thr Ala Gly Pro Leu
                    690                 695                 700
            Ser Thr Ala Trp Thr Pro Phe Asp Arg Lys Ile Val Gln Tyr Ala Gly
            705                 710                 715                 720
            Glu Ile Tyr Asn Tyr Asp Phe Pro Glu Tyr Gly Ala Gly Gln Pro Gly
                                725                 730                 735
            Ala Phe Gly Asp Ile Gln Ser Arg Thr Val Ser Ser Asp Leu Tyr
                            740                 745                 750
            Ala Asn Thr Asn Leu Val Leu Gln Arg Pro Lys Ala Gly Ala Ile His
                        755                 760                 765
            Val Pro Tyr Thr Gln Ala Pro Ser Gly Phe Glu Gln Trp Lys Lys Asp
                    770                 775                 780
            Lys Ala Pro Ser Leu Lys Phe Thr Ala Pro Phe Gly Cys Glu Ile Tyr
            785                 790                 795                 800
            Thr Asn Pro Ile Arg Ala Glu Asn Cys Ala Val Gly Ser Ile Pro Leu
                            805                 810                 815
            Ala Phe Asp Ile Pro Asp Ala Leu Phe Thr Arg Val Ser Glu Thr Pro
                        820                 825                 830
            Thr Leu Ser Ala Ala Glu Cys Thr Leu Asn Glu Cys Val Tyr Ser Ser
                        835                 840                 845
            Asp Phe Gly Gly Ile Ala Thr Val Lys Tyr Ser Ala Ser Lys Ser Gly
                    850                 855                 860
            Lys Cys Ala Val His Val Pro Ser Gly Thr Ala Thr Leu Lys Glu Ala
            865                 870                 875                 880
            Ala Val Glu Leu Thr Glu Gln Gly Ser Ala Thr Ile His Phe Ser Thr
                                885                 890                 895
            Ala Asn Ile His Pro Glu Phe Arg Leu Gln Ile Cys Thr Ser Tyr Val
                            900                 905                 910
            Thr Cys Lys Gly Asp Cys His Pro Pro Lys Asp His Ile Val Thr His
                        915                 920                 925
            Pro Gln Tyr His Ala Gln Thr Phe Thr Ala Ala Val Ser Lys Thr Ala
                    930                 935                 940
            Trp Thr Trp Leu Thr Ser Leu Leu Gly Gly Ser Ala Val Ile Ile Ile
            945                 950                 955                 960
            Ile Gly Leu Val Leu Ala Thr Ile Val Ala Met Tyr Val Leu Thr Asn
                                965                 970                 975
```

Gln Lys His Asn
            980

<210> SEQ ID NO 4
<211> LENGTH: 981
<212> TYPE: PRT
<213> ORGANISM: Venezuelan Equine Encephalitis Virus

<400> SEQUENCE: 4

Ser Leu Val Thr Thr Met Cys Leu Leu Ala Asn Val Thr Phe Pro Cys
1               5                   10                  15

Ala Gln Pro Pro Ile Cys Tyr Asp Arg Lys Pro Ala Glu Thr Leu Ala
            20                  25                  30

Met Leu Ser Val Asn Val Asp Asn Pro Gly Tyr Asp Glu Leu Leu Glu
        35                  40                  45

Ala Ala Val Lys Cys Pro Gly Ser Gly Gly Ser Ser Thr Glu Glu
    50                  55                  60

Leu Phe Asn Glu Tyr Lys Leu Thr Arg Pro Tyr Met Ala Arg Cys Ile
65                  70                  75                  80

Arg Cys Ala Val Gly Ser Cys His Ser Pro Ile Ala Ile Glu Ala Val
                85                  90                  95

Lys Ser Asp Gly His Asp Gly Tyr Val Arg Leu Gln Thr Ser Ser Gln
            100                 105                 110

Tyr Gly Leu Asp Ser Ser Gly Asn Leu Lys Gly Arg Thr Met Arg Tyr
        115                 120                 125

Asp Met His Gly Thr Ile Lys Glu Ile Pro Leu His Gln Val Ser Leu
    130                 135                 140

Tyr Thr Ser Arg Pro Cys His Ile Val Asp Gly His Gly Tyr Phe Leu
145                 150                 155                 160

Leu Ala Arg Cys Pro Ala Gly Asp Ser Ile Thr Met Glu Phe Lys Lys
                165                 170                 175

Asp Ser Val Arg His Ser Cys Ser Val Pro Tyr Glu Val Lys Phe Asn
            180                 185                 190

Pro Val Gly Arg Glu Leu Tyr Thr His Pro Pro Glu His Gly Val Glu
        195                 200                 205

Gln Ala Cys Gln Val Tyr Ala His Asp Ala Gln Asn Arg Gly Ala Tyr
    210                 215                 220

Val Glu Met His Leu Pro Gly Ser Glu Val Asp Ser Ser Leu Val Ser
225                 230                 235                 240

Leu Ser Gly Ser Ser Val Thr Val Thr Pro Pro Asp Gly Thr Ser Ala
                245                 250                 255

Leu Val Glu Cys Glu Cys Gly Gly Thr Lys Ile Ser Glu Thr Ile Asn
            260                 265                 270

Lys Thr Lys Gln Phe Ser Gln Cys Thr Lys Lys Glu Gln Cys Arg Ala
        275                 280                 285

Tyr Arg Leu Gln Asn Asp Lys Trp Val Tyr Asn Ser Asp Lys Leu Pro
    290                 295                 300

Lys Ala Ala Gly Ala Thr Leu Lys Gly Lys Leu His Val Pro Phe Leu
305                 310                 315                 320

Leu Ala Asp Gly Lys Cys Thr Val Pro Leu Ala Pro Glu Pro Met Ile
                325                 330                 335

Thr Phe Gly Phe Arg Ser Val Ser Leu Lys Leu His Pro Lys Asn Pro
            340                 345                 350

Thr Tyr Leu Ile Thr Arg Gln Leu Ala Asp Glu Pro His Tyr Thr His

```
             355                 360                 365
Glu Leu Ile Ser Glu Pro Ala Val Arg Asn Phe Thr Val Thr Glu Lys
370                 375                 380

Gly Trp Glu Phe Val Trp Gly Asn His Pro Pro Lys Arg Phe Trp Ala
385                 390                 395                 400

Gln Glu Thr Ala Pro Gly Asn Pro His Gly Leu Pro His Glu Val Ile
                405                 410                 415

Thr His Tyr Tyr His Arg Tyr Pro Met Ser Thr Ile Leu Gly Leu Ser
            420                 425                 430

Ile Cys Ala Ala Ile Ala Thr Val Ser Val Ala Ser Thr Trp Leu
        435                 440                 445

Phe Cys Arg Ser Arg Val Ala Cys Leu Thr Pro Tyr Arg Leu Thr Pro
    450                 455                 460

Asn Ala Arg Ile Pro Phe Cys Leu Ala Val Leu Cys Cys Ala Arg Thr
465                 470                 475                 480

Ala Arg Ala Glu Thr Thr Trp Glu Ser Leu Asp His Leu Trp Asn Asn
                485                 490                 495

Asn Gln Gln Met Phe Trp Ile Gln Leu Leu Ile Pro Leu Ala Ala Leu
                500                 505                 510

Ile Val Val Thr Arg Leu Leu Arg Cys Val Cys Cys Val Pro Phe
        515                 520                 525

Leu Val Met Ala Gly Ala Ala Gly Ala Gly Ala Tyr Glu His Ala Thr
530                 535                 540

Thr Met Pro Ser Gln Ala Gly Ile Ser Tyr Asn Thr Ile Val Asn Arg
545                 550                 555                 560

Ala Gly Tyr Ala Pro Leu Pro Ile Ser Ile Thr Pro Thr Lys Ile Lys
                565                 570                 575

Leu Ile Pro Thr Val Asn Leu Glu Tyr Val Thr Cys His Tyr Lys Thr
                580                 585                 590

Gly Met Asp Ser Pro Ala Ile Lys Cys Cys Gly Ser Gln Glu Cys Thr
            595                 600                 605

Pro Thr Tyr Arg Pro Asp Glu Gln Cys Lys Val Phe Thr Gly Val Tyr
        610                 615                 620

Pro Phe Met Trp Gly Gly Ala Tyr Cys Phe Cys Asp Thr Glu Asn Thr
625                 630                 635                 640

Gln Val Ser Lys Ala Tyr Val Met Lys Ser Asp Asp Cys Leu Ala Asp
                645                 650                 655

His Ala Glu Ala Tyr Lys Ala His Thr Ala Ser Val Gln Ala Phe Leu
            660                 665                 670

Asn Ile Thr Val Gly Glu His Ser Ile Val Thr Thr Val Tyr Val Asn
        675                 680                 685

Gly Glu Thr Pro Val Asn Phe Asn Gly Val Lys Ile Thr Ala Gly Pro
    690                 695                 700

Leu Ser Thr Ala Trp Thr Pro Phe Asp Arg Lys Ile Val Gln Tyr Ala
705                 710                 715                 720

Gly Glu Ile Tyr Asn Tyr Asp Phe Pro Glu Tyr Gly Ala Gly Gln Pro
                725                 730                 735

Gly Ala Phe Gly Asp Ile Gln Ser Arg Thr Val Ser Ser Ser Asp Leu
            740                 745                 750

Tyr Ala Asn Thr Asn Leu Val Leu Gln Arg Pro Lys Ala Gly Ala Ile
        755                 760                 765

His Val Pro Tyr Thr Gln Ala Pro Ser Gly Phe Glu Gln Trp Lys Lys
    770                 775                 780
```

```
Asp Lys Ala Pro Ser Leu Lys Phe Thr Ala Pro Phe Gly Cys Glu Ile
785                 790                 795                 800

Tyr Thr Asn Pro Ile Arg Ala Glu Asn Cys Ala Val Gly Ser Ile Pro
                805                 810                 815

Leu Ala Phe Asp Ile Pro Asp Ala Leu Phe Thr Arg Val Ser Glu Thr
            820                 825                 830

Pro Thr Leu Ser Ala Ala Glu Cys Thr Leu Asn Glu Cys Val Tyr Ser
        835                 840                 845

Ser Asp Phe Gly Gly Ile Ala Thr Val Lys Tyr Ser Ala Ser Lys Ser
850                 855                 860

Gly Lys Cys Ala Val His Val Pro Ser Gly Thr Ala Thr Leu Lys Glu
865                 870                 875                 880

Ala Ala Val Glu Leu Thr Glu Gln Gly Ser Ala Thr Ile His Phe Ser
                885                 890                 895

Thr Ala Asn Ile His Pro Glu Phe Arg Leu Gln Ile Cys Thr Ser Tyr
            900                 905                 910

Val Thr Cys Lys Gly Asp Cys His Pro Pro Lys Asp His Ile Val Thr
        915                 920                 925

His Pro Gln Tyr His Ala Gln Thr Phe Thr Ala Ala Val Ser Lys Thr
    930                 935                 940

Ala Trp Thr Trp Leu Thr Ser Leu Leu Gly Gly Ser Ala Val Ile Ile
945                 950                 955                 960

Ile Ile Gly Leu Val Leu Ala Thr Ile Val Ala Met Tyr Val Leu Thr
                965                 970                 975

Asn Gln Lys His Asn
            980

<210> SEQ ID NO 5
<211> LENGTH: 11543
<212> TYPE: DNA
<213> ORGANISM: Artificial Sequence
<220> FEATURE:
<223> OTHER INFORMATION: Genomic RNA expression Vector including
      Luciferase gene nucleotide

<400> SEQUENCE: 5
ttctcatgtt tgacagctta tcatcgatgc accgtgcatg ccgattggtg gaagtaaggt      60
ggtacgatcg tgccttatta ggaaggcaac agacaggtct gacatggatt ggacgaacca    120
ctgaattccg cattgcagag ataattgtat ttaagtgcct agctcgatac aataaacgcc    180
atttgaccat tcaccacatt ggtgtgcacc tccaataggc ggcgcatgag agaagcccag    240
accaattacc tacccaaaat ggagaaagtt cacgttgaca tcgaggaaga cagcccattc    300
ctcagagctt tgcagcggag cttcccgcag tttgaggtag aagccaagca ggtcactgat    360
aatgaccatg ctaatgccag agcgttttcg catctggctt caaaactgat cgaaacggag    420
gtggacccat ccgacacgat ccttgacatt ggaagtgcgc cgcccgcag aatgtattct    480 aagcacaagt atcattgtat ctgtccgatg agatgtgcgg aagatccgga cagattgtat    540
aagtatgcaa ctaagctgaa gaaaaactgt aaggaaataa ctgataagga attggacaag    600
aaaatgaagg agctcgccgc cgtcatgagc gaccctgacc tggaaactga gactatgtgc    660
ctccacgacg acgagtcgtg tcgctacgaa gggcaagtcg ctgtttacca ggatgtatac    720
gcggttgacg gaccgacaag tctctatcac caagccaata agggagttag agtcgcctac    780
tggataggct ttgacaccac ccctttttatg tttaagaact ggctggagc atatccatca    840
```

```
tactctacca actgggccga cgaaaccgtg ttaacggctc gtaacatagg cctatgcagc    900
tctgacgtta tggagcggtc acgtagaggg atgtccattc ttagaaagaa gtatttgaaa    960
ccatccaaca atgttctatt ctctgttggc tcgaccatct accacgagaa gagggactta   1020
ctgaggagct ggcacctgcc gtctgtattt cacttacgtg gcaagcaaaa ttacacatgt   1080
cggtgtgaga ctatagttag ttgcgacggg tacgtcgtta aaagaatagc tatcagtcca   1140
ggcctgtatg ggaagccttc aggctatgct gctacgatgc accgcgaggg attcttgtgc   1200
tgcaaagtga cagacacatt gaacggggag agggtctctt ttcccgtgtg cacgtatgtg   1260
ccagctacat tgtgtgacca atgactggc atactggcaa cagatgtcag tgcggacgac   1320
gcgcaaaaac tgctggttgg gctcaaccag cgtatagtcg tcaacggtcg cacccagaga   1380
aacaccaata ccatgaaaaa ttacctttg cccgtagtgg cccaggcatt tgctaggtgg   1440
gcaaggaat ataaggaaga tcaagaagat gaaaggccac taggactacg agatagacag   1500
ttagtcatgg ggtgttgttg ggcttttaga aggcacaaga taacatctat ttataagcgc   1560
ccggataccc aaaccatcat caaagtgaac agcgatttcc actcattcgt gctgcccagg   1620
ataggcagta acacattgga gatcgggctg agaacaagaa tcaggaaaat gttagaggag   1680
cacaaggagc cgtcacctct cattaccgcc gaggacgtac aagaagctaa gtgcgcagcc   1740
gatgaggcta aggaggtgcg tgaagccgag gagttgcgcg cagctctacc acctttggca   1800
gctgatgttg aggagcccac tctggaagcc gatgtcgact tgatgttaca agaggctggg   1860
gccggctcag tggagacacc tcgtggcttg ataaaggtta ccagctacga tggcgaggac   1920
aagatcggct cttacgctgt gctttctccg caggctgtac tcaagagtga aaaattatct   1980
tgcatccacc ctctcgctga acaagtcata gtgataacac actctggccg aaaagggcgt   2040
tatgccgtgg aaccatacca tggtaaagta gtggtgccag agggacatgc aatacccgtc   2100
caggactttc aagctctgag tgaaagtgcc accattgtgt acaacgaacg tgagttcgta   2160
aacaggtacc tgcaccatat tgccacacat ggaggagcgc tgaacactga tgaagaatat   2220
tacaaaactg tcaagcccag cgagcacgac ggcgaatacc tgtacgacat cgacaggaaa   2280
cagtgcgtca agaaagaact agtcactggg ctagggctca caggcgagct ggtggatcct   2340
cccttccatg aattcgccta cgagagtctg agaacacgac cagccgctcc ttaccaagta   2400
ccaaccatag gggtgtatgg cgtgccagga tcaggcaagt ctggcatcat taaaagcgca   2460
gtcaccaaaa agatctagt ggtgagcgcc aagaaagaaa actgtgcaga aattataagg   2520
gacgtcaaga aaatgaaagg gctggacgtc aatgccagaa ctgtggactc agtgctcttg   2580
aatggatgca acacccccgt agagaccctg tatattgacg aagcttttgc ttgtcatgca   2640
ggtactctca gagcgctcat agccattata agacctaaaa aggcagtgct ctgcggggat   2700
cccaaacagt gcggtttttt taacatgatg tgcctgaaag tgcattttaa ccacgagatt   2760
tgcacacaag tcttccacaa aagcatctct cgccgttgca ctaaatctgt gacttcggtc   2820
gtctcaacct tgttttacga caaaaaaatg agaacgacga atccgaaaga gactaagatt   2880
gtgattgaca ctaccggcag taccaaacct aagcaggacg atctcattct cacttgtttc   2940
agagggtggg tgaagcagtt gcaaatagat tacaaaggca acgaaataat gacggcagct   3000
gcctctcaag ggctgacccg taaggtgtg tatgccgttc ggtacaaggt gaatgaaaat   3060
cctctgtacg cacccaccct agaacatgtg aacgtcctac tgacccgcac ggaggaccgc   3120
atcgtgtgga aaaacactagc cggcgaccca tggataaaaa cactgactgc caagtaccct   3180
gggaatttca ctgccacgat agaggagtgg caagcagagc atgatgccat catgaggcac   3240
```

```
atcttggaga gaccggaccc taccgacgtc ttccagaata aggcaaacgt gtgttgggcc    3300
aaggctttag tgccggtgct gaagaccgct ggcatagaca tgaccactga acaatggaac    3360
actgtggatt attttgaaac ggacaaagct cactcagcag agatagtatt gaaccaacta    3420
tgcgtgaggt tctttggact cgatctggac tccggtctat tttctgcacc cactgttccg    3480
ttatccatta ggaataatca ctgggataac tccccgtcgc ctaacatgta cgggctgaat    3540
aaagaagtgg tccgtcagct ctctcgcagg tacccacaac tgcctcgggc agttgccact    3600
ggaagagtct atgacatgaa cactggtaca ctgcgcaatt atgatccgcg cataaaccta    3660
gtacctgtaa acagaagact gcctcatgct ttagtcctcc accataatga acacccacag    3720
agtgactttt cttcattcgt cagcaaattg aagggcagaa ctgtcctggt ggtcggggaa    3780
aagttgtccg tcccaggcaa aatggttgac tggttgtcag accggcctga ggctaccttc    3840
agagctcggc tggatttagg catcccaggt gatgtgccca aatatgacat aatatttgtt    3900
aatgtgagga cccatataa ataccatcac tatcagcagt gtgaagacca tgccattaag    3960
cttagcatgt tgaccaagaa agcttgtctg catctgaatc ccggcggaac ctgtgtcagc    4020
ataggttatg gttacgctga cagggccagc gaaagcatca ttggtgctat agcgcggcag    4080
ttcaagtttt cccgggtatg caaaccgaaa tcctcacttg aagagacgga agttctgttt    4140
gtattcattg ggtacgatcg caaggcccgt acgcacaatc cttacaagct ttcatcaacc    4200
ttgaccaaca tttatacagg ttccagactc cacgaagccg gatgtgcacc ctcatatcat    4260
gtggtgcgag gggatattgc cacggccacc gaaggagtga ttataaatgc tgctaacagc    4320
aaaggacaac ctggcggagg ggtgtgcgga gcgctgtata agaaattccc ggaaagcttc    4380
gatttacagc cgatcgaagt aggaaaagcg cgactggtca aggtgcagc taaacatatc    4440
attcatgccg taggaccaaa cttcaacaaa gtttcggagg ttgaaggtga caaacagttg    4500
gcagaggctt atgagtccat cgctaagatt gtcaacgata caattacaa gtcagtagcg    4560
attccactgt tgtccaccgg catctttttc gggaacaaag atcgactaac ccaatcattg    4620
aaccatttgc tgacagcttt agacaccact gatgcagatg tagccatata ctgcagggac    4680
aagaaatggg aaatgactct caaggaagca gtggctagga gagaagcagt ggaggagata    4740
tgcatatccg acgactcttc agtgacagaa cctgatgcag agctggtgag ggtgcatccg    4800
aagagttctt tggctggaag gaagggctac agcacaagcg atggcaaaac tttctctat    4860
ttggaaggga ccaagtttca ccaggcggcc aaggatatag cagaaattaa tgccatgtgg    4920
cccgttgcaa cggaggccaa tgagcaggta tgcatgtata tcctcggaga aagcatgagc    4980
agtattaggt cgaaatgccc cgtcgaagag tcggaagcct ccacaccacc tagcacgctg    5040
ccttgcttgt gcatccatgc catgactcca gaaagagtac agcgcctaaa agcctcacgt    5100
ccagaacaaa ttactgtgtg ctcatccttt ccattgccga agtatagaat cactggtgtg    5160
cagaagatcc aatgctccca gcctatattg ttctcaccga agtgcctgc gtatattcat    5220
ccaaggaagt atctcgtgga acaccaccg gtagacgaga ctccggagcc atcggcagag    5280
aaccaatcca cagaggggac acctgaacaa ccaccactta taaccgagga tgagaccagg    5340
actagaacgc tgagccgat catcatcgaa gaggaagaag aggatagcat aagtttgctg    5400
tcagatggcc cgacccacca ggtgctgcaa gtcgaggcag acattcacgg gccgccctct    5460
gtatctagct catcctggtc cattcctcat gcatccgact ttgatgtgga cagtttatcc    5520
atacttgaca ccctggaggg agctagcgtg accagcgggg caacgtcagc cgagactaac    5580
```

-continued

```
tcttacttcg caaagagtat ggagtttctg gcgcgaccgg tgcctgcgcc tcgaacagta    5640
ttcaggaacc ctccacatcc cgctccgcgc acaagaacac cgtcacttgc acccagcagg    5700
gcctgctcga gaaccagcct agtttccacc ccgccaggcg tgaatagggt gatcactaga    5760
gaggagctcg aggcgcttac cccgtcacgc actcctagca ggtcggtctc gagaaccagc    5820
ctggtctcca acccgccagg cgtaaatagg gtgattacaa gagaggagtt tgaggcgttc    5880
gtagcacaac aacaatgacg gtttgatgcg ggtgcataca tcttttcctc cgacaccggt    5940
caagggcatt tacaacaaaa atcagtaagg caaacggtgc tatccgaagt ggtgttggag    6000
aggaccgaat tggagatttc gtatgccccg cgcctcgacc aagaaaaaga agaattacta    6060
cgcaagaaat tacagttaaa tcccacacct gctaacagaa gcagataccc gtccaggaag    6120
gtggagaaca tgaaagccat aacagctaga cgtattctgc aaggcctagg gcattatttg    6180
aaggcagaag gaaaagtgga gtgctaccga accctgcatc ctgttccttt gtattcatct    6240
agtgtgaacc gtgcctttc aagccccaag gtcgcagtgg aagcctgtaa cgccatgttg    6300
aaagagaact ttccgactgt ggcttcttac tgtattattc cagagtacga tgcctatttg    6360
gacatggttg acggagcttc atgctgctta gacactgcca gttttttgccc tgcaaagctg    6420 cgcagcttc caaagaaaca ctcctatttg gaacccacaa tacgatcggc agtgccttca    6480
gcgatccaga acacgctcca gaacgtcctg gcagctgcca caaaaagaaa ttgcaatgtc    6540
acgcaaatga gagaattgcc cgtattggat tcggcggcct ttaatgtgga atgcttcaag    6600
aaatatgcgt gtaataatga atattgggaa acgtttaaag aaaacccccat caggcttact    6660 gaagaaaacg tggtaaatta cattaccaaa ttaaaaggac caaaagctgc tgctctttt    6720 gcgaagacac ataatttgaa tatgttgcag gacataccaa tggacaggtt tgtaatggac    6780
ttaaagagag acgtgaaagt gactccagga acaaaacata ctgaagaacg gcccaaggta    6840
caggtgatcc aggctgccga tccgctagca acagcgtatc tgtgcggaat ccaccgagag    6900
ctggttagga gattaaatgc ggtcctgctt ccgaacattc atacactgtt tgatatgtcg    6960
gctgaagact ttgacgctat tatagccgag cacttccagc ctggggattg tgttctggaa    7020
actgacatcg cgtcgtttga taaaagtgag gacgacgcca tggctctgac cgcgttaatg    7080
attctggaag acttaggtgt ggacgcagag ctgttgacgc tgattgaggc ggctttcggc    7140
gaaatttcat caatacattt gcccactaaa actaaattta aattcggagc catgatgaaa    7200
tctggaatgt tcctcacact gtttgtgaac acagtcatta acattgtaat cgcaagcaga    7260
gtgttgagag aacggctaac cggatcacca tgtgcagcat tcattggaga tgacaatatc    7320
gtgaaaggag tcaaatcgga caaattaatg gcagacaggt gcgccacctg gttgaatatg    7380
gaagtcaaga ttatagatgc tgtggtgggc gagaaagcgc cttatttctg tggagggttt    7440 atttgtgtg actccgtgac cggcacagcg tgccgtgtgg cagacccccct aaaaaggctg    7500 tttaagcttg gcaaacctct ggcagcagac gatgaacatg atgatgacag agaagggca    7560 ttgcatgaag agtcaacacg ctggaaccga gtgggtattc tttcagagct gtgcaaggca    7620
gtagaatcaa ggtatgaaac cgtaggaact tccatcatag ttatggccat gactactcta    7680
gctagcagtg ttaaatcatt cagctacctg agaggggccc ctataactct ctacggctaa    7740
cctgaatgga ctacgacata gtctagtccg ccaagatggt cttcacactc gaagatttcg    7800
ttggggactg gcgacagaca gccggctaca acctggacca agtccttgaa cagggaggtg    7860
tgtccagttt gtttcagaat ctcggggtgt ccgtaactcc gatccaaagg attgtcctga    7920
gcggtgaaaa tgggctgaag atcgacatcc atgtcatcat cccgtatgaa ggtctgagcg    7980
```

```
gcgaccaaat gggccagatc gaaaaaattt ttaaggtggt gtaccctgtg gatgatcatc      8040
actttaaggt gatcctgcac tatggcacac tggtaatcga cggggttacg ccgaacatga      8100
tcgactattt cggacggccg tatgaaggca tcgccgtgtt cgacggcaaa aagatcactg      8160
taacagggac cctgtggaac ggcaacaaaa ttatcgacga gcgcctgatc aaccccgacg      8220
gctccctgct gttccgagta accatcaacg gagtgaccgg ctggcggctg tgcgaacgca      8280
ttctggcgta aatacagcag caattggcaa gctgcttaca tagaactcgc ggcgattggc      8340
atgccgcctt aaaattttta ttttattttt cttttctttt ccgaatcgga ttttgttttt      8400
aatatttcaa aaaaaaaaa aaaaaaaaa aaaaaaaaa aaaaaaaaa aaaaaaaaa            8460 aaatcgcgac agacatgata agatacattg atgagtttgg acaaaccaca actagaatgc      8520
agtgaaaaaa atgctttatt tgtgaaattt gtgatgctat tgctttattt gtaaccatta      8580
taagctgcaa taaacaagtt aacaacaaca attgcattca ttttatgttt caggttcagg      8640
gggaggtgtg ggaggttttt taggacccgg ctaggctggc ggggttgcct tactggttag      8700
cagaatgaat caccgatacg cgagcgaacg tgaagcgact gctgctgcaa aacgtctgcg      8760
acctgagcaa caacatgaat ggtcttcggt ttccgtgttt cgtaaagtct ggaaacgcgg      8820
aagtcagcgc cctgcaccat tatgttccgg atctgcatcg caggatgctg ctggctaccc      8880
tgtggaacac ctcacatctgt attaacgaag cgctggcatt gaccctgagt gatttttctc      8940
tggtcccgcc gcatccatac cgccagttgt ttaccctcac aacgttccag taaccgggca      9000
tgttcatcat cagtaacccg tatcgtgagc atcctctctc gtttcatcgg tatcattacc      9060
cccatgaaca gaaatccccc ttacacggag gcatcagtga ccaaacagga aaaaaccgcc      9120
cttaacatgg cccgctttat cagaagccag acattaacgc ttctggagaa actcaacgag      9180
ctggacgcgg atgaacaggc agacatctgt gaatcgcttc acgaccacgc tgatgagctt      9240
taccgcagct gcctcgcgcg tttcggtgat gacggtgaaa acctctgaca catgcagctc      9300
ccggagacgg tcacagcttg tctgtaagcg gatgccggga gcagacaagc ccgtcagggc      9360
gcgtcagcgg gtgttggcgg gtgtcggggc gcagccatga cccagtcacg tagcgatagc      9420
ggagtgtata ctggcttaac tatgcggcat cagagcagat tgtactgaga gtgcaccata      9480
tgcggtgtga ataccgcac agatgcgtaa ggagaaaata ccgcatcagg cgctcttccg      9540
cttcctcgct cactgactcg ctgcgctcgg tcgttcggct gcggcgagcg gtatcagctc      9600
actcaaaggc ggtaatacgg ttatccacag aatcagggga taacgcagga agaacatgt      9660 gagcaaaagg ccagcaaaag gccaggaacc gtaaaaaggc cgcgttgctg gcgttttcc       9720 ataggctccg ccccctgac gagcatcaca aaaatcgacg ctcaagtcag gtggcgaa       9780 acccgacagg actataaaga taccaggcgt ttccccctgg aagctccctc gtgcgctctc      9840
ctgttccgac cctgccgctt accggatacc tgtccgcctt tctcccttcg ggaagcgtgg      9900
cgctttctca tagctcacgc tgtaggtatc tcagttcggt gtaggtcgtt cgctccaagc      9960
tgggctgtgt gcacgaaccc cccgttcagc ccgaccgctg cgccttatcc ggtaactatc     10020
gtcttgagtc aacccggta agacacgact tatcgccact ggcagcagcc actggtaaca     10080
ggattagcag agcgaggtat gtaggcggtg ctacagagtt cttgaagtgg tggcctaact     10140
acggctacac tagaaggaca gtatttggta tctgcgctct gctgaagcca gttaccttcg     10200
gaaaaagagt tggtagctct tgatccggca aacaaaccac cgctggtagc ggtggttttt     10260
ttgtttgcaa gcagcagatt acgcgcagaa aaaaaggatc tcaagaagat cctttgatct     10320
```

```
tttctacggg gtctgacgct cagtggaacg aaaactcacg ttaagggatt ttggtcatga    10380
gattatcaaa aaggatcttc acctagatcc ttttaaatta aaaatgaagt tttaaatcaa    10440
tctaaagtat atatgagtaa acttggtctg acagttacca atgcttaatc agtgaggcac    10500
ctatctcagc gatctgtcta tttcgttcat ccatagttgc ctgactcccc gtcgtgtaga    10560
taactacgat acgggagggc ttaccatctg gccccagtgc tgcaatgata ccgcgagacc    10620
cacgctcacc ggctccagat ttatcagcaa taaaccagcc agccggaagg gccgagcgca    10680
gaagtggtcc tgcaacttta tccgcctcca tccagtctat taattgttgc cgggaagcta    10740
gagtaagtag ttcgccagtt aatagtttgc gcaacgttgt tgccattgct gcaggcatcg    10800
tggtgtcacg ctcgtcgttt ggtatggctt cattcagctc cggttcccaa cgatcaaggc    10860
gagttacatg atcccccatg ttgtgcaaaa aagcggttag ctccttcggt cctccgatcg    10920
ttgtcagaag taagttggcc gcagtgttat cactcatggt tatggcagca ctgcataatt    10980
ctcttactgt catgccatcc gtaagatgct tttctgtgac tggtgagtac tcaaccaagt    11040
cattctgaga atagtgtatg cggcgaccga gttgctcttg cccggcgtca acacgggata    11100
ataccgcgcc acatagcaga actttaaaag tgctcatcat tggaaaacgt tcttcggggc    11160
gaaaactctc aaggatctta ccgctgttga tccagttc gatgtaaccc actcgtgcac    11220
ccaactgatc ttcagcatct tttactttca ccagcgtttc tgggtgagca aaaacaggaa    11280
ggcaaaatgc cgcaaaaaag gaataagggc gacacggaa atgttgaata ctcatactct    11340
tcctttttca atattattga agcatttatc agggttattg tctcatgagc ggatacatat    11400
ttgaatgtat ttagaaaaat aaacaaatag gggttccgcg cacatttccc cgaaaagtgc    11460
cacctgacgt ctaagaaacc attattatca tgacattaac ctataaaaat aggcgtatca    11520
cgaggccctt tcgtcttcaa gaa                                           11543
```

<210> SEQ ID NO 6
<211> LENGTH: 11597
<212> TYPE: DNA
<213> ORGANISM: Artificial Sequence
<220> FEATURE:
<223> OTHER INFORMATION: Genomic RNA expression Vector including
      Luciferase gene with Multiple cloning sites

<400> SEQUENCE: 6

```
ttctcatgtt tgacagctta tcatcgatgc accgtgcatg ccgattggtg gaagtaaggt      60
ggtacgatcg tgccttatta ggaaggcaac agacaggtct gacatggatt ggacgaacca    120
ctgaattccg cattgcagag ataattgtat ttaagtgcct agctcgatac aataaacgcc    180
atttgaccat tcaccacatt ggtgtgcacc tccaataggc ggcgcatgag agaagcccag    240
accaattacc tacccaaaat ggagaaagtt cacgttgaca tcgaggaaga cagcccattc    300
ctcagagctt tgcagcggag cttcccgcag tttgaggtag aagccaagca ggtcactgat    360
aatgaccatg ctaatgccag agcgttttcg catctggctt caaaactgat cgaaacggag    420
gtggacccat ccgacacgat ccttgacatt ggaagtgcgc ccgcccgcag aatgtattct    480
aagcacaagt atcattgtat ctgtccgatg agatgtgcgg aagatccgga cagattgtat    540
aagtatgcaa ctaagctgaa gaaaaactgt aaggaaataa ctgataagga attggacaag    600
aaaatgaagg agctcgccgc cgtcatgagc gaccctgacc tggaaactga gactatgtgc    660
ctccacgacg acgagtcgtg tcgctacgaa gggcaagtcg ctgtttacca ggatgtatac    720
gcggttgacg gaccgacaag tctctatcac caagccaata agggagttag agtcgcctac    780
```

```
tggataggct ttgacaccac ccctttatg tttaagaact tggctggagc atatccatca    840
tactctacca actgggccga cgaaaccgtg ttaacggctc gtaacatagg cctatgcagc   900
tctgacgtta tggagcggtc acgtagaggg atgtccattc ttagaaagaa gtatttgaaa   960
ccatccaaca atgttctatt ctctgttggc tcgaccatct accacgagaa gagggactta  1020
ctgaggagct ggcacctgcc gtctgtattt cacttacgtg gcaagcaaaa ttacacatgt  1080
cggtgtgaga ctatagttag ttgcgacggg tacgtcgtta aaagaatagc tatcagtcca  1140
ggcctgtatg ggaagccttc aggctatgct gctacgatgc accgcgaggg attcttgtgc  1200
tgcaaagtga cagacacatt gaacggggag agggtctctt ttcccgtgtg cacgtatgtg  1260
ccagctacat tgtgtgacca aatgactggc atactggcaa cagatgtcag tgcggacgac  1320
gcgcaaaaac tgctggttgg gctcaaccag cgtatagtcg tcaacggtcg cacccagaga  1380
aacaccaata ccatgaaaaa ttacctttg cccgtagtgg cccaggcatt tgctaggtgg  1440
gcaaaggaat ataaggaaga tcaagaagat gaaaggccac taggactacg agatagacag  1500
ttagtcatgg ggtgttgttg ggcttttaga aggcacaaga taacatctat ttataagcgc  1560
ccggataccc aaaccatcat caaagtgaac agcgatttcc actcattcgt gctgcccagg  1620
ataggcagta acacattgga gatcgggctg agaacaagaa tcaggaaaat gttagaggag  1680
cacaaggagc cgtcacctct cattaccgcc gaggacgtac aagaagctaa gtgcgcagcc  1740
gatgaggcta aggaggtgcg tgaagccgag gagttgcgcg cagctctacc acctttggca  1800
gctgatgttg aggagcccac tctggaagcc gatgtcgact tgatgttaca agaggctggg  1860
gccggctcag tggagacacc tcgtggcttg ataaaggtta ccagctacga tggcgaggac  1920
aagatcggct cttacgctgt gctttctccg caggctgtac tcaagagtga aaaattatct  1980
tgcatccacc ctctcgctga acaagtcata gtgataacac actctggccg aaaagggcgt  2040
tatgccgtgg aaccatacca tggtaaagta gtggtgccag agggacatgc aatacccgtc  2100
caggactttc aagctctgag tgaaagtgcc accattgtgt acaacgaacg tgagttcgta  2160
aacaggtacc tgcaccatat tgccacacat ggaggagcgc tgaacactga tgaagaatat  2220
tacaaaactg tcaagcccag cgagcacgac ggcgaatacc tgtacgacat cgacaggaaa  2280
cagtgcgtca agaaagaact agtcactggg ctagggctca caggcgagct ggtggatcct  2340
cccttccatg aattcgccta cgagagtctg agaacacgac cagccgctcc ttaccaagta  2400
ccaaccatag gggtgtatgg cgtgccagga tcaggcaagt ctggcatcat taaaagcgca  2460
gtcaccaaaa aagatctagt ggtgagcgcc aagaaagaaa actgtgcaga aattataagg  2520
gacgtcaaga aaatgaaagg gctggacgtc aatgccagaa ctgtggactc agtgctcttg  2580
aatggatgca acaccccgt agagaccctg tatattgacg aagcttttgc ttgtcatgca  2640
ggtactctca gagcgctcat agccattata agacctaaaa aggcagtgct ctgcggggat  2700
cccaaacagt gcggtttttt taacatgatg tgcctgaaag tgcattttaa ccacgagatt  2760
tgcacacaag tcttccacaa aagcatctct cgccgttgca ctaaatctgt gacttcggtc  2820
gtctcaacct tgttttacga caaaaaatg agaacgacga atccgaaaga gactaagatt  2880
gtgattgaca ctaccggcag taccaaacct aagcaggacg atctcattct cacttgtttc  2940
agagggtggg tgaagcagtt gcaaatagat tacaaaggca acgaaataat gacggcagct  3000
gcctctcaag gctgaccccg taaggtgtg tatgccgttc ggtacaaggt gaatgaaaat  3060
cctctgtacg cacccacctc agaacatgtg aacgtcctac tgacccgcac ggaggaccgc  3120
atcgtgtgga aaacactagc cggcgaccca tggataaaaa cactgactgc caagtaccct  3180
```

```
gggaatttca ctgccacgat agaggagtgg caagcagagc atgatgccat catgaggcac    3240
atcttggaga gaccggaccc taccgacgtc ttccagaata aggcaaacgt gtgttgggcc    3300
aaggctttag tgccggtgct gaagaccgct ggcatagaca tgaccactga acaatggaac    3360
actgtggatt attttgaaac ggacaaagct cactcagcag agatagtatt gaaccaacta    3420
tgcgtgaggt tctttggact cgatctggac tccggtctat tttctgcacc cactgttccg    3480
ttatccatta ggaataatca ctgggataac tccccgtcgc ctaacatgta cgggctgaat    3540
aaagaagtgg tccgtcagct ctctcgcagg tacccacaac tgcctcgggc agttgccact    3600
ggaagagtct atgacatgaa cactggtaca ctgcgcaatt atgatccgcg cataaaccta    3660
gtacctgtaa acagaagact gcctcatgct ttagtcctcc accaatgatga acacccacag    3720 agtgactttt cttcattcgt cagcaaattg aagggcagaa ctgtcctggt ggtcggggaa    3780
aagttgtccg tcccaggcaa atggttgac tggttgtcag accggcctga ggctaccttc    3840
agagctcggc tggatttagg catcccaggt gatgtgccca aatatgacat aatatttgtt    3900
aatgtgagga ccccatataa ataccatcac tatcagcagt gtgaagacca tgccattaag    3960
cttagcatgt tgaccaagaa agcttgtctg catctgaatc ccggcggaac ctgtgtcagc    4020
ataggttatg gttacgctga cagggccagc gaaagcatca ttggtgctat agcgcggcag    4080
ttcaagtttt cccgggtatg caaaccgaaa tcctcacttg aagagacgga agttctgttt    4140
gtattcattg ggtacgatcg caaggcccgt acgcacaatc cttacaagct ttcatcaacc    4200
ttgaccaaca tttatacagg ttccagactc cacgaagccg gatgtgcacc ctcatatcat    4260
gtggtgcgag gggatattgc cacggccacc gaaggagtga ttataaatgc tgctaacagc    4320
aaaggacaac ctggcggagg ggtgtgcgga gcgctgtata agaaattccc ggaaagcttc    4380
gatttacagc cgatcgaagt aggaaaagcg cgactggtca aaggtgcagc taaacatatc    4440
attcatgccg taggaccaaa cttcaacaaa gtttcggagg ttgaaggtga caaacagttg    4500
gcagaggctt atgagtccat cgctaagatt gtcaacgata caattacaa gtcagtagcg    4560 attccactgt tgtccaccgg catcttttcc gggaacaaag atcgactaac ccaatcattg    4620
aaccatttgc tgacagcttt agacaccact gatgcagatg tagccatata ctgcagggac    4680
aagaaatggg aaatgactct caaggaagca gtggctagga gagaagcagt ggaggagata    4740
tgcatatccg acgactcttc agtgacagaa cctgatgcag agctggtgag ggtgcatccg    4800
aagagttctt tggctggaag gaagggctac agcacaagcg atggcaaaac tttctctatat    4860 ttggaaggga ccaagtttca ccaggcggcc aaggatatag cagaaattaa tgccatgtgg    4920
cccgttgcaa cggaggccaa tgagcaggta tgcatgtata tcctcggaga aagcatgagc    4980
agtattaggt cgaaatgccc cgtcgaagag tcggaagcct ccacaccacc tagcacgctg    5040
ccttgcttgt gcatccatgc catgactcca gaaagagtac agcgcctaaa agcctcacgt    5100
ccagaacaaa ttactgtgtg ctcatccttt ccattgccga agtatagaat cactggtgtg    5160
cagaagatcc aatgctccca gcctatattg ttctcaccga aagtgcctgc gtatattcat    5220
ccaaggaagt atctcgtgga aacaccaccg gtagacgaga ctccggagcc atcggcagag    5280
aaccaatcca cagaggggac acctgaacaa ccaccactta taaccgagga tgagaccagg    5340
actagaacgc ctgagccgat catcatcgaa gaggaagaag aggatagcat aagtttgctg    5400
tcagatggcc cgacccacca ggtgctgcaa gtcgaggcag acattcacgg gccgcccctct    5460 gtatctagct catcctggtc cattcctcat gcatccgact ttgatgtgga cagtttatcc    5520
```

```
atacttgaca ccctggaggg agctagcgtg accagcgggg caacgtcagc cgagactaac    5580
tcttacttcg caaagagtat ggagtttctg gcgcgaccgg tgcctgcgcc tcgaacagta    5640
ttcaggaacc ctccacatcc cgctccgcgc acaagaacac cgtcacttgc acccagcagg    5700
gcctgctcga gaaccagcct agtttccacc ccgccaggcg tgaatagggt gatcactaga    5760
gaggagctcg aggcgcttac cccgtcacgc actcctagca ggtcggtctc gagaaccagc    5820
ctggtctcca acccgccagg cgtaaatagg gtgattacaa gagaggagtt tgaggcgttc    5880
gtagcacaac aacaatgacg gtttgatgcg ggtgcataca tcttttcctc cgacaccggt    5940
caagggcatt tacaacaaaa atcagtaagg caaacggtgc tatccgaagt ggtgttggag    6000
aggaccgaat tggagatttc gtatgccccg cgcctcgacc aagaaaaaga agaattacta    6060
cgcaagaaat tacagttaaa tcccacacct gctaacagaa gcagatacca gtccaggaag    6120
gtggagaaca tgaaagccat aacagctaga cgtattctgc aaggcctagg gcattatttg    6180
aaggcagaag gaaagtggag gtgctaccga accctgcatc ctgttccttt gtattcatct    6240
agtgtgaacc gtgccttttc aagccccaag gtcgcagtgg aagcctgtaa cgccatgttg    6300
aaagagaact ttccgactgt ggcttcttac tgtattattc cagagtacga tgcctatttg    6360
gacatggttg acgagcttc atgctgctta gacactgcca gtttttgccc tgcaaagctg    6420
cgcagctttc caagaaaca ctcctatttg gaacccacaa tacgatcggc agtgccttca    6480
gcgatccaga acacgctcca gaacgtcctg gcagctgcca caaaagaaa ttgcaatgtc    6540 acgcaaatga gagaattgcc cgtattggat tcggcggcct ttaatgtgga atgcttcaag    6600
aaatatgcgt gtaataatga atattgggaa acgtttaaag aaaaccccat caggcttact    6660
gaagaaaacg tggtaaatta cattaccaaa ttaaaggac caaaagctgc tgctctttt    6720 gcgaagacac ataatttgaa tatgttgcag gacataccaa tggacaggtt tgtaatggac    6780
ttaaagagag acgtgaaagt gactccagga acaaaacata ctgaagaacg gcccaaggta    6840
caggtgatcc aggctgccga tccgctagca acagcgtatc tgtgcggaat ccaccgagag    6900
ctggttagga gattaaatgc ggtcctgctt ccgaacattc atacactgtt tgatatgtcg    6960
gctgaagact ttgacgctat tatagccgag cacttccagc ctggggattg tgttctggaa    7020
actgacatcg cgtcgtttga taaaagtgag gacgacgcca tggctctgac cgcgttaatg    7080
attctggaag acttaggtgt ggacgcagag ctgttgacgc tgattgaggc ggctttcggc    7140
gaaatttcat caatacattt gcccactaaa actaaattta aattcggagc catgatgaaa    7200
tctggaatgt tcctcacact gtttgtgaac acagtcatta acattgtaat cgcaagcaga    7260
gtgttgagag aacggctaac cggatcacca tgtgcagcat tcattggaga tgacaatatc    7320
gtgaaaggag tcaaatcgga caaattaatg gcagacaggt gcgccacctg gttgaatatg    7380
gaagtcaaga ttatagatgc tgtggtgggc gagaaagcgc cttatttctg tggagggttt    7440
attttgtgtg actccgtgac cggcacagcg tgccgtgtgg cagaccccct aaaaaggctg    7500
tttaagcttg gcaaacctct ggcagcagac gatgaacatg atgatgacag agaagggca    7560 ttgcatgaag agtcaacacg ctggaaccga gtgggtattc tttcagagct gtgcaaggca    7620
gtagaatcaa ggtatgaaac cgtaggaact tccatcatag ttatggccat gactactcta    7680
gctagcagtg ttaaatcatt cagctacctg agaggggccc ctataactct ctacggctaa    7740
cctgaatgga ctacgacata gtctagtccg ccaagggcgc gccttcgaag gccggccgtt    7800
taaacatggt cttcacactc gaagatttcg ttggggactg gcgacagaca gccggctaca    7860
acctggacca agtccttgaa cagggaggtg tgtccagttt gtttcagaat ctcggggtgt    7920
```

```
ccgtaactcc gatccaaagg attgtcctga gcggtgaaaa tgggctgaag atcgacatcc    7980
atgtcatcat cccgtatgaa ggtctgagcg gcgaccaaat gggccagatc gaaaaaattt    8040
ttaaggtggt gtaccctgtg gatgatcatc actttaaggt gatcctgcac tatggcacac    8100
tggtaatcga cggggttacg ccgaacatga tcgactattt cggacggccg tatgaaggca    8160
tcgccgtgtt cgacggcaaa aagatcactg taacagggac cctgtggaac ggcaacaaaa    8220
ttatcgacga gcgcctgatc aaccccgacg gctccctgct gttccgagta accatcaacg    8280
gagtgaccgg ctggcggctg tgcgaacgca ttctggcgta agcggccgcc ctgcagggcg    8340
atcgcataca gcagcaattg gcaagctgct tacatagaac tcgcggcgat tggcatgccg    8400
ccttaaaatt tttattttat ttttcttttc ttttccgaat cggattttgt tttaatatt    8460
tcaaaaaaaa aaaaaaaaaa aaaaaaaaaa aaaaaaaaa aaaaaaaaa aaaaaatcg    8520
cgacagacat gataagatac attgatgagt ttggacaaac cacaactaga atgcagtgaa    8580
aaaaatgctt tatttgtgaa atttgtgatg ctattgcttt atttgtaacc attataagct    8640
gcaataaaca agttaacaac aacaattgca ttcattttat gtttcaggtt caggggagg    8700
tgtgggaggt tttttaggac ccggctaggc tggcggggtt gccttactgg ttagcagaat    8760
gaatcaccga tacgcgagcg aacgtgaagc gactgctgct gcaaaacgtc tgcgacctga    8820
gcaacaacat gaatggtctt cggtttccgt gtttcgtaaa gtctggaaac gcggaagtca    8880
gcgccctgca ccattatgtt ccggatctgc atcgcaggat gctgctggct accctgtgga    8940
acacctacat ctgtattaac gaagcgctgg cattgaccct gagtgatttt tctctggtcc    9000
cgccgcatcc ataccgccag ttgtttaccc tcacaacgtt ccagtaaccg gcatgttca    9060
tcatcagtaa cccgtatcgt gagcatcctc tctcgtttca tcggtatcat tacccccatg    9120
aacagaaatc ccccttacac ggaggcatca gtgaccaaac aggaaaaaac cgcccttaac    9180
atggcccgct ttatcagaag ccagacatta acgcttctgg agaaactcaa cgagctggac    9240
gcggatgaac aggcagacat ctgtgaatcg cttcacgacc acgctgatga gctttaccgc    9300
agctgcctcg cgcgtttcgg tgatgacggt gaaaacctct gacacatgca gctcccggag    9360
acggtcacag cttgtctgta gcggatgcc gggagcagac aagcccgtca gggcgcgtca    9420
gcgggtgttg gcgggtgtcg gggcgcagcc atgacccagt cacgtagcga tagcggagtg    9480
tatactggct taactatgcg gcatcagagc agattgtact gagagtgcac catatgcggt    9540
gtgaaatacc gcacagatgc gtaaggagaa ataccgcat caggcgctct tccgcttcct    9600
cgctcactga ctcgctgcgc tcggtcgttc ggctgcggcg agcggtatca gctcactcaa    9660
aggcggtaat acggttatcc acagaatcag gggataacgc aggaaagaac atgtgagcaa    9720
aaggccagca aaaggccagg aaccgtaaaa aggccgcgtt gctggcgttt ttccataggc    9780
tccgccccc tgacgagcat cacaaaaatc gacgctcaag tcagaggtgg cgaaacccga    9840
caggactata aagataccag gcgtttcccc ctggaagctc cctcgtgcgc tctcctgttc    9900
cgaccctgcc gcttaccgga tacctgtccg cctttctccc ttcgggaagc gtggcgcttt    9960
ctcatagctc acgctgtagg tatctcagtt cggtgtaggt cgttcgctcc aagctgggct   10020
gtgtgcacga accccccgtt cagcccgacc gctgcgcctt atccggtaac tatcgtcttg   10080
agtccaaccc ggtaagacac gacttatcgc cactggcagc agccactggt aacaggatta   10140
gcagagcgag gtatgtaggc ggtgctacag agttcttgaa gtggtggcct aactacggct   10200
acactagaag gacagtattt ggtatctgcg ctctgctgaa gccagttacc ttcggaaaaa   10260
```

```
gagttggtag ctcttgatcc ggcaaacaaa ccaccgctgg tagcggtggt ttttttgttt    10320
gcaagcagca gattacgcgc agaaaaaaag gatctcaaga agatcctttg atcttttcta    10380
cggggtctga cgctcagtgg aacgaaaact cacgttaagg gattttggtc atgagattat    10440
caaaaaggat cttcacctag atccttttaa attaaaaatg aagttttaaa tcaatctaaa    10500
gtatatatga gtaaacttgg tctgacagtt accaatgctt aatcagtgag gcacctatct    10560
cagcgatctg tctatttcgt tcatccatag ttgcctgact ccccgtcgtg tagataacta    10620
cgatacggga gggcttacca tctggcccca gtgctgcaat gataccgcga gacccacgct    10680
caccggctcc agatttatca gcaataaacc agccagccgg aagggccgag cgcagaagtg    10740
gtcctgcaac tttatccgcc tccatccagt ctattaattg ttgccgggaa gctagagtaa    10800
gtagttcgcc agttaatagt ttgcgcaacg ttgttgccat tgctgcaggc atcgtggtgt    10860
cacgctcgtc gtttggtatg gcttcattca gctccggttc ccaacgatca aggcgagtta    10920
catgatcccc catgttgtgc aaaaaagcgg ttagctcctt cggtcctccg atcgttgtca    10980
gaagtaagtt ggccgcagtg ttatcactca tggttatggc agcactgcat aattctctta    11040
ctgtcatgcc atccgtaaga tgcttttctg tgactggtga gtactcaacc aagtcattct    11100
gagaatagtg tatgcggcga ccgagttgct cttgcccggc gtcaacacgg gataataccg    11160
cgccacatag cagaacttta aaagtgctca tcattggaaa acgttcttcg gggcgaaaac    11220
tctcaaggat cttaccgctg ttgagatcca gttcgatgta acccactcgt gcacccaact    11280
gatcttcagc atcttttact ttcaccagcg tttctgggtg agcaaaaaca ggaaggcaaa    11340
atgccgcaaa aaagggaata agggcgacac ggaaatgttg aatactcata ctcttccttt    11400
ttcaatatta ttgaagcatt tatcagggtt attgtctcat gagcggatac atatttgaat    11460
gtatttagaa aaataaacaa ataggggttc cgcgcacatt tccccgaaaa gtgccacctg    11520
acgtctaaga aaccattatt atcatgacat taacctataa aaataggcgt atcacgaggc    11580
cctttcgtct tcaagaa                                                  11597

<210> SEQ ID NO 7
<211> LENGTH: 21
<212> TYPE: DNA
<213> ORGANISM: Artificial Sequence
<220> FEATURE:
<223> OTHER INFORMATION: VEEV_gblock2_fwd primer

<400> SEQUENCE: 7
tcattcagct acctgagagg g                                              21

<210> SEQ ID NO 8
<211> LENGTH: 25
<212> TYPE: DNA
<213> ORGANISM: Artificial Sequence
<220> FEATURE:
<223> OTHER INFORMATION: VEEV_gblock2_rev primer

<400> SEQUENCE: 8
aaataaaaat tttaaggcgg catgc                                          25

<210> SEQ ID NO 9
<211> LENGTH: 60
<212> TYPE: DNA
<213> ORGANISM: Artificial Sequence
<220> FEATURE:
<223> OTHER INFORMATION: VEEV_Oligo1_fwd primer

<400> SEQUENCE: 9
```

```
<210> SEQ ID NO 10
<211> LENGTH: 100
<212> TYPE: DNA
<213> ORGANISM: Artificial Sequence
<220> FEATURE:
<223> OTHER INFORMATION: VEEV_Oligo2_rev primer

<400> SEQUENCE: 10
catcaatgta tcttatcatg tctgtcgcga tttttttttt tttttttttt tttttttttt      60
tttttttttt tttttttttt tttttgaaat attaaaaaca                            100

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
ccggcccgga ccgacaagtc tctatcacc                                        29

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
ggccgggggc ccctctcagg tagctgaatg                                       30
```

ALPHAVIRUS REPLICON PARTICLE

CROSS REFERENCE TO RELATED APPLICATIONS

This application is a continuation of U.S. patent application Ser. No. 16/225,181, filed Dec. 19, 2018, which claims the benefit of U.S. provisional Patent Application No. 62/608,213 filed on Dec. 20, 2017, the entire contents of which are incorporated by reference herein.

INCORPORATION BY REFERENCE OF SEQUENCE LISTING

The content of the electronically submitted sequence listing, file name: Q268156_sequence listing as filed; size: 53,768 bytes; and date of creation: Sep. 18, 2024, filed herewith, is incorporated herein by reference in its entirety.

TECHNICAL FIELD

The present invention relates to an alphavirus replicon particle that can be used as a gene delivery system.

BACKGROUND ART

Gene therapy is designed to introduce genetic material into cells to compensate for abnormal genes or to make a beneficial protein. If a mutated gene causes a necessary protein to be faulty or missing, gene therapy may be able to introduce a normal copy of the gene to restore the function of the protein.

Gene therapy is an emerging field in medical and pharmaceutical sciences because of its potential in treating chronic diseases like cancer, viral infections, myocardial infarctions, and genetic disorders, etc.

A gene that is inserted directly into a cell usually does not function. Instead, a carrier called a vector is genetically engineered to deliver the gene. Certain viruses are often used as vectors because they can deliver the new gene by infecting the cell. The viruses are modified so they can't cause disease when used in people. Some types of virus, such as retroviruses, integrate their genetic material (including the new gene) into a chromosome in the human cell. Other viruses, such as adenoviruses, introduce their gene into the nucleus of the cell, but the gene is not integrated into the chromosome.

The vector can be injected directly into a specific tissue where it is taken up by individual cells or given intravenously (by IV) in the body. Alternately, a sample of the patient's cells can be removed and exposed to the vector in a laboratory setting. The cells containing the vector are then returned to the patient. If the treatment is successful, the new gene delivered by the vector will make a functioning protein. (ghr.nlm.nih.gov/primer/therapy/procedures, Int J Pharm Investig. 2013 January-March; 3 (1): 1-7.)

Alphaviruses comprise a set of genetically, structurally, and serologically related mosquito-borne viruses of the Togaviridae family. The alphaviruses include Eastern Equine Encephalitis Virus (EEEV), Venezuelan Equine Encephalitis Virus (VEEV), Everglades Virus, Mucambo Virus, Pixuna Virus, Western Equine Encephalitis Virus (WEEV), Sindbis Virus, Semliki Forest Virus, Middleburg Virus, Chikungunya Virus (CHIKV), O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands J virus, Fort Morgan Virus, Ndumu Virus, and Buggy Creek Virus. Structural subunits containing a single viral protein, capsid, associate with the RNA genome in an icosahedral nucleocapsid. In the virion, the capsid is surrounded by a lipid envelope covered with a regular array of transmembrane protein spikes, each of which consists of a heterodimeric complex of two glycoproteins, E1 and E2.

An alphavirus replicon particle (ARP) is produced in cells or cultures and incorporates a "replicon" that can express non-alphavirus genes within the virion shell comprising alphavirus structural proteins and membrane lipid.

Alphavirus replicon particles are described in U.S. Pat. No. 7,045,335, WO 2004/085660 and Virology 239, 389-401, 1997. Processes for their manufacture are described in U.S. Pat. No. 7,078,218, the contents of the documents cited in this paragraph are incorporated by reference.

Clinical application of gene therapy is still limited because of lack of suitable methods for proper introduction of genes into cells and therefore, this is an area of interest for many researchers. To achieve successful gene therapy, development of proper gene delivery systems could be one of the most important factors (Int. J Pharm Investig. 2013 January-March; 3 (1): 1-7).

CITATION LIST

Patent Literature

[PTL 1]
U.S. Pat. No. 7,045,335
[PTL 2]
WO2004/085660
[PTL 3]
U.S. Pat. No. 7,078,218

Non Patent Literature

[NPL 1]
Int J Pharm Investig. 2013 January-March; 3 (1): 1-7
[NPL 2]
Virology 239, 389-401, 1997

SUMMARY OF INVENTION

The present invention relates to a gene delivery system comprising an improved alphavirus replicon particle.

In one aspect, an alphavirus replicon particle (ARP), which comprises
  (i) alphavirus structural proteins comprising capsid and/or envelope, and
  (ii) an alphavirus replicon comprising a polynucleotide encoding alphavirus non-structural proteins nsp1, nsp2, nsp3 and nsp4 and at least one gene of interest
  wherein at least one of capsid, E3 and E2 in the envelope comprise one or more amino acid alteration but E1 in the envelope comprises no amino acid alteration.

In one aspect, the invention provides an ARP, wherein the virus structural protein has one or more alterations in the alphavirus capsid protein Nuclear Localization Signal (NLS).

In one aspect, the alphavirus capsid protein is an EEEV, WEEV, VEEV, CHIKV, Ross River virus, or Barmah Forest virus capsid protein. In various embodiments of the above aspects or any other aspect of the invention described herein, the one or more alterations is in an NLS at amino acids 67-70 of an EEEV capsid protein; at amino acids 67-70 of an WEEV capsid protein; at amino acids 64-68 of an VEEV capsid protein; at amino acids 62-69 of a CHIKV capsid protein; at amino acids 71-74 of a Ross River virus capsid protein; or at amino acids 64-68 of a Barmah Forest virus capsid protein.

In various embodiments of the above aspects or any other aspect of the invention described herein, the alteration is a substitution in a charged amino acid of the NLS or basic charged amino acid of the NLS. In some embodiments, the charged amino acid or basic charged amino acid is lysine or arginine. In certain embodiments, the lysine or arginine is substituted with a non-lysine or non-arginine amino acids. In specific embodiments, the lysine or arginine is substituted with asparagine or alanine.

In various embodiments of the above aspects or any other aspect of the invention described herein, the EEEV virus capsid protein NLS is altered at amino acid 67. In particular embodiments, the EEEV virus capsid protein NLS has a substitution K67N.

In various embodiments of the above aspects or any other aspect of the invention described herein, the WEEV virus capsid protein NLS is altered at one or more of amino acids 67, 68, and 69. In particular embodiments, the WEEV capsid protein NLS comprises K67N, K68N, and/or K69N.

In various embodiments of the above aspects or any other aspect of the invention described herein, the VEEV capsid protein NLS is altered at one or more of amino acids 64, 65, and 67. In particular embodiments, the VEEV virus capsid protein NLS comprises K64N, K65A or K65N, and/or K67A or K67N.

In various embodiments of the above aspects or any other aspect of the invention described herein, the Ross River virus capsid protein NLS is altered at one or more of amino acids 71, 72, 73, and 74. In particular embodiments, the Ross River virus capsid protein NLS comprises R71N, R72N, R73N, and/or R74N.

In various embodiments of the above aspects or any other aspect of the invention described herein, the Barmah Forest virus capsid protein NLS is altered at one or more of amino acids 64, 65, 67, and 68. In particular embodiments, the Barmah Forest virus capsid protein NLS comprises K64A, K65A or K65N, K67A, K67N, K68A and/or K68N.

Alteration in the capsid NLS is described in detail in US Patent Publication Nos. 2014-170186 or 2017-073377. The contents of these publications are herein incorporated by reference.

In one aspect, alphavirus E2 protein may have a non-lysine residue (e.g., asparagine) at the amino acid position corresponding to amino acid 234 in the CHIKV E2 protein and/or a modification at the amino acid position corresponding to amino acid 251 in the CHIKV E2 protein that destabilizes the E2 protein during viral budding.

In one aspect, the alphavirus E3 protein may comprise an alteration/mutation in the amino acid sequence at the furin site (Arg-X-X-Arg) (SEQ ID NO: 13).

The term "Arg-X-X-Arg" (SEQ ID NO: 13) indicates the minimal cleavage site of furin and "X-X" includes any combination of two amino acids. Example of the alteration to the amino acid sequence at furin site includes the alteration to Ile-Glu/Asp-Gly-Arg, Asp-Asp-Asp-Asp-Lys (SEQ ID NO: 14) or Ser-Gly-Gly-Gly-Ser (SEQ ID NO: 15). Details regarding furin site alteration are described in US Patent Publication Nos. 2016-0040134 and 2016-0200775 (the cited documents are herein incorporated by reference).

For example, VEEV CT83 strain has a furin site of RKRR (SEQ ID NO: 16) at the end of its E3 region and RKRR (SEQ ID NO: 16) may be replaced with SGGGS (SEQ ID NO: 15).

According to the present invention, the alphavirus replicon comprises nucleotide encoding alphavirus nonstructural proteins nsp1, nsp2, nsp3 and nsp4, and at least one gene of interest. The alphavirus nonstructural proteins may be those derived from the same alphavirus as the alphavirus from which the structural proteins are derived. The alphavirus nonstructural proteins may be those derived from an alphavirus different from the alphavirus from which the structural proteins are derived (chimeric alphavirus replicon particle).

For example, ARPs comprising the alphavirus structural proteins derived from CHIKV and alphavirus replicon comprising nucleotides encoding VEEV nsp1, nsp2, nsp3 and nsp4 and a gene of interest may be provided according to the present invention.

In one aspect, the present invention provides an alphavirus replicon particle (ARP), which comprises
 (i) CHIKV structural proteins comprising capsid and/or envelope, and
 (ii) a VEEV replicon comprising a polynucleotide encoding VEEV non-structural proteins nsp1, nsp2, nsp3 and nsp4 and at least one gene of interest.

The gene of interest may be chosen from a wide variety of sequences derived from any desired source, e.g., viruses, prokaryotes, eukaryotes, archaea. Examples of categories of gene of interest include, for example, immunogens, including antigenic proteins, cytokines, toxins, therapeutic proteins, enzymes, antisense sequences, and immune response modulators.

In another aspect, the invention provides a method for preparing alphavirus replicon particles, comprising the steps of co-transfecting cells with
 i) a vector comprising a polynucleotide encoding alphavirus non-structural protein nsp1, nsp2, nsp3 and nsp4, and at least one gene of interest,
 ii) a vector comprising a polynucleotide encoding an alphavirus capsid protein, and
 iii) a vector comprising a polynucleotide encoding an alphavirus E3-E2-6K-E1,
 wherein at least one of the capsid, E3 and E2 comprises one or more amino acid alteration but E1 comprises no amino acid alteration,
 culturing the transfected cells, and
 purifying the ARPs from the cell culture.

In general, nucleotides encoding alphavirus structural proteins comprise those encoding E1, E2, 6k and E3. Upon expression of the wild type virus structural proteins, 6K and E3 are naturally cleaved during the process of assemble and removed from the ARPs. The mature wild type ARPs may comprise capsid, E1 and E2 proteins. When one or more alterations of the amino acid sequences are introduced in, for example, the furin site of E3 protein, E3 may not be cleaved and contained in the ARPs. In the present specification and claims, "viral structural proteins" refers not only those having 6k and/or E3 but also those not having 6K and/or E3.

Representative ARPs wherein the alphavirus is CHIKV or VEEV are exemplified by FIG. 1.

In one aspect, the present invention provides a chimeric alphavirus replicon particle,
 (i) CHIKV structural proteins comprising capsid and/or envelope, and
 (ii) a VEEV replicon comprising a polynucleotide encoding VEEV non-structural proteins nsp1, nsp2, nsp3 and nsp4 and at least one gene of interest.

BRIEF DESCRIPTION OF DRAWINGS

FIG. 7 shows TC83_CMV_E3gp_helper 2P vector

FIG. 11 shows VEEV_pBR322_MCS_NLuc_Putative vector.

FIG. 12 shows result of western blotting of purified VEE virus replicon particles.

DESCRIPTION OF EMBODIMENTS

Definitions

Figure 1:
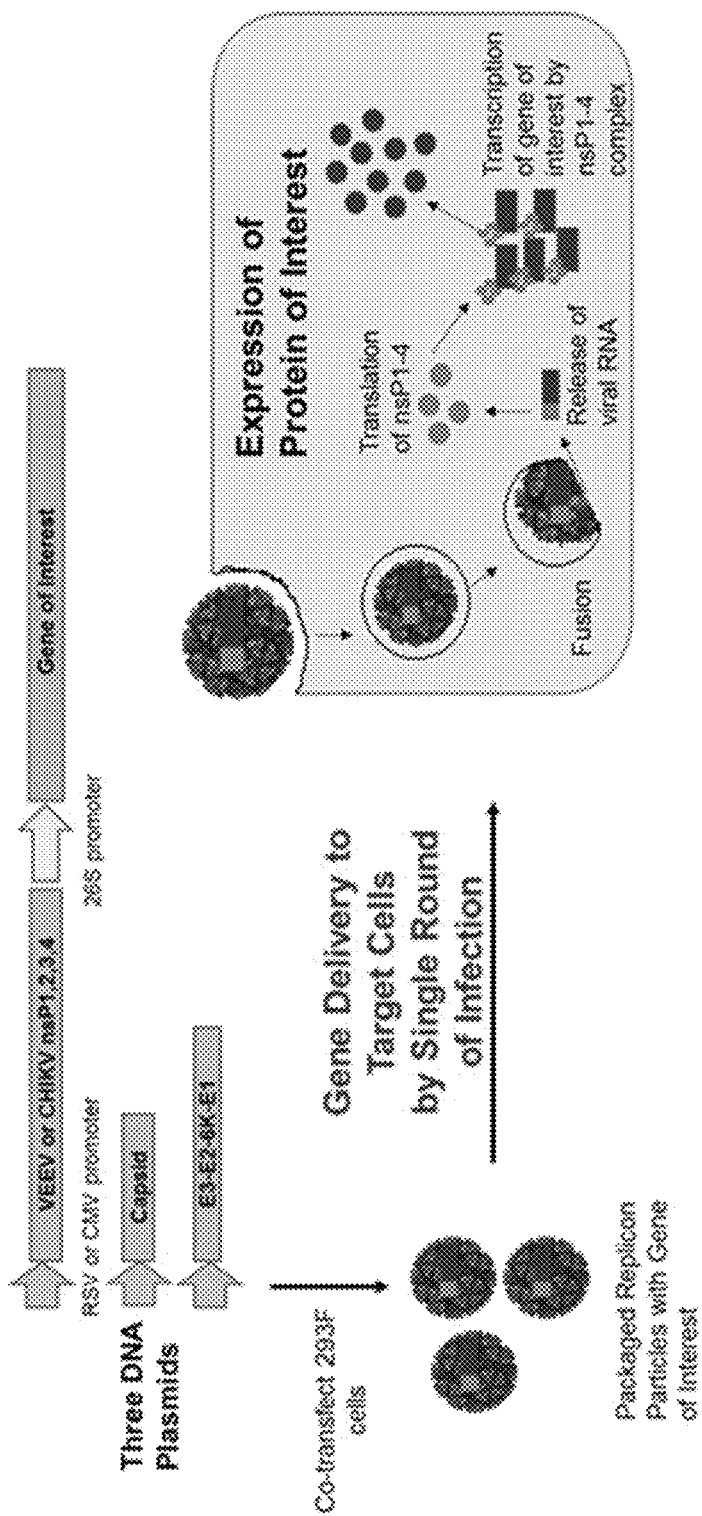
FIG. 1 shows a schematic protocol for producing ARPs.

As used herein "alphavirus" is meant to refer to RNA-containing viruses that belong to the Togaviridae family of viruses. Exemplary Togaviridae viruses include but are not limited to Eastern Equine Encephalitis Virus (EEEV), Venezuelan Equine Encephalitis Virus (VEEV), Everglades Virus, Mucambo Virus, Pixuna Virus, Western Equine Encephalitis Virus (WEEV), Sindbis Virus, Semliki Forest Virus, Middleburg Virus, Chikungunya Virus (CHIKV), O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands J virus, Fort Morgan Virus, Ndumu Virus, Buggy Creek Virus and Ockelbo virus.

By "alphavirus structural protein" is meant a polypeptide or fragment thereof having at least about 80% amino acid sequence identity to a naturally occurring viral capsid or envelope protein. In one embodiment, the alphavirus structural protein has at least about 85%, 90%, 95% or greater amino acid sequence identity with Eastern Equine Encephalitis Virus (EEEV), Venezuelan Equine Encephalitis Virus (VEEV), Everglades Virus, Mucambo Virus, Pixuna Virus, Western Equine Encephalitis Virus (WEEV), Sindbis Virus, Semliki Forest Virus, Middleburg Virus, Chikungunya Virus (CHIKV), O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands J virus, Fort Morgan Virus, Ndumu Virus, and Buggy Creek Virus. Wild type amino acid sequences of alphavirus structural proteins can be obtained from GenBank.

In specific embodiments, the alphavirus is a CHIKV, for example CHIKV strain 37997 or LR2006 OPY-1. In other embodiments, the alphavirus is a VEEV, for example VEEV strain TC-83.

By "an alphavirus replicon" is meant an RNA molecule which can direct its own amplification in vivo in a target cell. The replicon encodes the polymerase(s) which catalyze RNA amplification (nsp1, nsp2, nsp3, nsp4) and contains cis RNA sequences required for replication which are recognized and utilized by the encoded polymerase(s). An alphavirus replicon typically contains the following ordered elements: 5' UTR, sequences which encode alphavirus nonstructural proteins (nsp1, nsp2, nsp3, nsp4), 3' UTR, and a poly A signal. An alphavirus replicon also contains one or more viral sub-genomic promoters directing the expression of the gene of interest. Those sequences may have one or more mutations taught in a prior art.

By "alphavirus replicon particle" (ARP) is meant an alphavirus replicon packaged with alphavirus structural proteins. ARP does not contain polynucleotide encoding any of the alphavirus structural proteins.

By "agent" is meant any small molecule chemical compound, antibody, nucleic acid molecule, or polypeptide, or fragments thereof.

As used herein, the term "adjuvant" is meant to refer to a compound that, when used in combination with a specific immunogen in a formulation, will augment, alter or modify the resultant immune response. In certain embodiments, the adjuvant is used in combination with a ARP. Modification of the immune response includes intensification or broadening the specificity of either or both antibody and cellular immune responses. Modification of the immune response can also mean decreasing or suppressing certain antigen-specific immune responses. In one embodiment, the adjuvant is Ribi adjuvant.

By "ameliorate" is meant decrease, suppress, attenuate, diminish, arrest, or stabilize the development or progression of a disease or a symptom thereof.

By "alteration" is meant a change in an amino acid or nucleotide at a specified position with reference to a polypeptide sequence or polynucleotide sequence. As used herein, an alteration includes a substitution, deletion, or insertion of an amino acid or nucleotide at a specified position of a polypeptide or polynucleotide. In some embodiments, an alteration in an alphavirus capsid protein nuclear localization signal includes substitution of a charged amino acid (e.g., lysine or arginine) with an uncharged amino acid (e.g., alanine or asparagine, or any amino acid except a basic charged amino acid such as lysine or arginine).

By "alteration" is meant a change (increase or decrease) with reference to the expression levels or activity of a gene or polypeptide as detected by standard art known methods, such as those described herein. As used herein, an alteration includes a 10%, 25%, 50%, 75%, 100% or greater change in expression levels. An alteration includes a 10-, 20-, 50-, 70-, 80-, 90-, 100-, 200-, 500-, 1000-fold or greater change in expression levels.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ.

By "effective amount" is meant the amount of an agent required to ameliorate the symptoms of a disease relative to an untreated patient. The effective amount of active compound(s) used to practice the present invention for prevention or treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "marker" is meant any protein or polynucleotide having an alteration in expression level or activity that is associated with a disease or disorder.

As used herein, "nuclear localization signal" or "NLS" is an amino acid sequence that, when present on the surface of a polypeptide, targets the polypeptide to the nucleus of the cell. NLS sequences are known in the art. See, for example, Goldfarb, D., and N. Michaud (1991) Trends Cell Biol. 1, 20-24; Gorlich, D., and I. W. Mattaj (1996) Science 271, 1513-1518). In one embodiment, an NLS includes one or more short sequences of positively charged amino acids, such as lysines or arginines. Consensus sequences for NLS include K-K/R-X-K/R (Schneider, J. et al. (1988) Cell 54,117-125) and two clusters of basic amino acids, separated by a spacer of about 10 amino acids, e.g., KR [PAATKK-AGQA] KKKK (SEQ ID NO: 17) (Dingwall et al.,/Cell Biol. 107 (3): 841-9). With reference to the alphavirus amino acid sequences of the invention, NLS are present at amino acids 67-70 of an EEEV capsid protein (KRKK) (SEQ ID NO: 18); at amino acids 67-70 of an WEEV capsid protein (KKKK) (SEQ ID NO: 19); at amino acids 64-68 of a VEEV capsid protein (KKPKK) (SEQ ID NO: 20); at amino acids 62-69 of a CHIKV capsid protein (RRNRKNKK) (SEQ ID NO: 21); at amino acids 71-74 of a Ross River virus capsid protein (RKKK) (SEQ ID NO: 22); and at amino acids 64-68 of a Barmah Forest virus capsid protein (KKPKK) (SEQ ID NO: 20). For example, K64N of VEEV TC83 capsid protein may be employed.

As used herein, "obtaining" as in "obtaining an agent" includes synthesizing, purchasing, or otherwise acquiring the agent.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or there between.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e<"3> and e<"100> indicating a closely related sequence.

By "structural polyprotein" is meant a composite amino acid molecule comprising at least two separable polypeptides that contribute to a viral capsid or envelope. In one embodiment, the polypeptides are susceptible to cleavage with a viral enzyme (e.g., capsid autoproteinase and signalases).

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any compositions or methods provided herein can be combined with one or more of any of the other compositions and methods provided herein.

Alphavirus Replicon

The alphavirus replicon can, when delivered to an eukaryote cell, lead to the production of multiple daughter RNAs by transcription from itself (via an antisense copy which it generates from itself). The alphavirus replicon can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded protein, or may be transcribed to provide further transcripts with the same sense as the delivered RNA which are translated to provide in situ expression of the protein. The overall result of this sequence of transcriptions is a huge amplification in the number of the introduced replicon RNAs and so the encoded protein becomes a major polypeptide product of the cells.

According to the present invention, the alphavirus replicon comprises polynucleotides that encode non-structural proteins n1, n2, n3 and n4, and at least one gene of interest. Alphavirus replicon does not encode any of the alphavirus structural proteins.

The alphavirus nonstructural proteins may be wild type proteins derived from one of the above discussed alphaviruses or may have one or more alterations in the wild type amino acid sequences. Alterations of alphavirus nonstructural proteins are disclosed in various prior art references and the art can choose a suitable alphavirus nonstructural protein based on those publicly known information.

Alphavirus replicons are well known in the art and may be employed any of those previously disclosed replicons (for example, Virology. 1997 Dec. 22; 239 (2): 389-401., WO2009/131604, WO2011/005799, WO2012/031043, WO2014/1270493 and WO2015/095167, the contents of the cited documents are herein incorporated by reference).

Alphavirus Structural Proteins

The ARP has alphavirus structural proteins of capsid and envelope proteins. Preferably, the alphavirus structural proteins comprise the capsid protein and E2 and E1 proteins of the envelope, and may also have E3 protein of the envelope. According to the present invention, at least one of capsid and envelope has at least one alteration that enhances ARP expression in mammalian cells.

In one embodiment, the alphavirus structural proteins includes at least an alphavirus capsid protein having a non-lysine residue (e.g., alanine or asparagine) at an amino acid position corresponding to a lysine residue in the alphavirus capsid protein NLS and/or a non-arginine residue (e.g., alanine or asparagine) at an amino acid position corresponding to an arginine residue in the alphavirus capsid protein NLS. In specific embodiments, the alphavirus capsid protein is a WEEV CBA87 strain capsid protein having one or more of the alterations K67N, K68N, and K69N. In certain embodiments, the alphavirus capsid protein is a VEEV TC83 strain capsid protein having one or more of the alterations K64N, K65A, K65N, K67A, and K67N. In some embodiments, the alphavirus capsid protein is a EEEV PE-6 strain capsid protein having an alteration K67N. In particular embodiments, the alphavirus capsid protein is CHIKV Strain 37997 capsid protein having one or more of the alterations R62A, R63A, R65A, K66A, K68A, and K69A; the alphavirus capsid protein is a Ross River Virus capsid protein having one or more of the alterations R71N, K72N, K73N, and K74N; the alphavirus capsid protein is a Barmah Forest Virus capsid protein having one or more of the alterations K64A, K64N, K65A, K65N, K67A, K67N, K68A and K68N. The wild type capsid protein amino acid sequences of the above-discussed alphaviruses are available at GenBank.

In one embodiment, the alphavirus E2 protein has a non-lysine residue (e.g., asparagine) at the amino acid position corresponding to amino acid 234 in the CHIKV E2 protein and/or a modification at the amino acid position corresponding to amino acid 251 in the CHIKV E2 protein that destabilizes the E2 protein during viral budding.

In one embodiment, the polynucleotide encoding alphavirus E3 may be modified to comprise an alteration/mutation to the amino acid sequence at the furin site (Arg-X-X-Arg) (SEQ ID NO: 13).

The term "Arg-X-X-Arg" (SEQ ID NO: 13) indicates the minimal cleavage site of furin and "X-X" includes any combination of two amino acids. Example of the alteration to the amino acid sequence at furin site includes the alteration to Ile-Glu/Asp-Gly-Arg, Asp-Asp-Asp-Asp-Lys (SEQ ID NO: 14) or Ser-Gly-Gly-Gly-Ser (SEQ ID NO: 15). Detailed descriptions described in US Patent Publication Nos. 2016-0040134 and 2016-0200775 (the cited documents are herein incorporated by reference).

For example, VEEV CT83 strain has a furin site include RKRR (SEQ ID NO: 16) at the end of its E3 region and the polynucleotide sequence encoding RKRR (SEQ ID NO: 16) may be replaced with that encoding SGGGS (SEQ ID NO: 15).

In some embodiments of the invention, proteins may comprise mutations containing alterations which produce silent substitutions, additions, or deletions, but do not alter the properties or activities of the encoded protein or how the proteins are made.

Method of Preparing ARPs

ARPs may be prepared by procedures that are known to the art. Exemplified procedure for producing ARPs is disclosed in Virology 239, 389-401, 1997, the contents of the cited document is herein incorporated by reference.

In general, ARPs may be produced by co-transfection of suitable host cells with a vector encoding an alphavirus replicon, i.e. a vector comprising a polynucleotide encoding nsp1, nsp2, nsp3 and nsp4, and a gene of interest; and at least one helper vector encoding the alphavirus virus structural proteins. Preferably, cells are co-transfected with a vector encoding an alphavirus replicon, a vector encoding a capsid protein and a vector encoding envelope proteins.

In particular, the invention provides a method for preparing alphavirus replicon particles, comprising the steps of co-transfecting cells with
   i) a vector comprising a polynucleotide encoding alphavirus non-structural protein nsp1, nsp2, nsp3 and nsp4, and at least one gene of interest, ii) a vector comprising a polynucleotide encoding an alphavirus capsid protein, and iii) a vector comprising a polynucleotide encoding an alphavirus E3-E2-6K-E1, wherein at least one of the capsid, E3 and E2 comprises one or more amino acid alteration but E1 comprises no amino acid alteration, culturing the transfected cells, and purifying the ARPs from the cell culture.

Those skilled in the field of molecular biology will understand that any of a wide variety of expression systems may be used to produce ARPs. The precise cell to be co-transfected (host cells) is not critical to the invention. ARP may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, COS cells). Such cells are available from a wide range of sources (e.g., the American Type Culture Collection, Rockland, Md.; also, see, e.g., Ausubel et al., supra). Non limiting examples of insect cells are, *Spodoptera frugiperda* (Sf) cells, e.g., Sf9, Sf21, *Trichoplusia ni* cells, e.g., High Five cells, and *Drosophila* S2 cells. Examples of fungi (including yeast) host cells are *S. cerevisiae, Kluyveromyces lactis* (*K lactis*), species of *Candida* including *C. albicans* and *C. glabrata, Aspergillus nidulans, Schizosaccharomyces pombe* (*S. pombe*), *Pichia pastoris*, and *Yarrowia lipolytica*. Examples of mammalian cells are COS cells, baby hamster kidney cells, mouse L cells, LNCaP cells, Chinese hamster ovary (CHO) cells, human embryonic kidney (HEK) cells, African green monkey cells, CV1 cells, Hela cells, MDCK cells, Vero and Hep-2 cells. *Xenopus laevis* oocytes, or other cells of amphibian origin, may also be used. Prokaryotic host cells include bacterial cells, for example, *E. coli, B. subtilis*, and mycobacteria.

Methods of obtaining polynucleotides encoding said proteins are known in the art. For example, the gene encoding a specific alphavirus protein, e.g., a CHIKV, WEEV, EEEV, VEEV, Ross River virus, or Barmah Forest virus structural protein can be isolated by RT-PCR from polyadenylated mRNA extracted from cells which had been infected with said virus. The resulting product gene can be cloned as a polynucleotide insert into a vector.

The term "vector" refers to the means by which a nucleic acid sequence can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Typically, the nucleic acid molecule to be expressed is "operably linked" to a promoter and/or enhancer, and is subject to transcription regulatory control by the promoter and/or enhancer.

The method of transfection and the choice of expression vehicle will depend on the host system selected. Transfection methods are described, e.g., in Ausubel et al. (supra); expression vehicles may be chosen from those provided, e.g., in Cloning Vectors: A Laboratory Manual (P. H. Pouwels et al., 1985, Supp. 1987) The references cited in this paragraph are herein incorporated by reference.

A variety of expression systems exist for the production of the ARPs of the invention. Expression vectors useful for producing such ARPs include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Constructs and/or vectors used herein comprise alphavirus polynucleotides that encode structural proteins, including envelope proteins or capsid protein as described herein. Also, constructs and/or vectors used herein comprise alphavirus polynucleotides that encode nonstructural proteins nsp1, nsp2, nsp3 and nsp4 and a gene of interest.

The vector may be, for example, a phage, plasmid, viral, or retroviral vector. The constructs and/or vectors that comprise the nucleotides should be operatively linked to an appropriate promoter, such as the CMV promoter, phage lambda PL promoter, the *E. coli* lac, phoA and tac promoters, the SV40 early and late promoters, and promoters of retroviral LTRs are non-limiting examples. Other suitable promoters will be known to the skilled artisan depending on the host cell and/or the rate of expression desired. The expression constructs will further contain sites for transcription initiation, termination, and, in the transcribed region, a ribosome-binding site for translation. The coding portion of the transcripts expressed by the constructs will preferably include a translation initiating codon at the beginning and a termination codon appropriately positioned at the end of the polypeptide to be translated.

Vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus), herpesvirus, and retrovirus. Other vectors that can be used with the invention comprise vectors for use in bacteria, which comprise pQE70, PQE60 and pQE-9, pBluescript vectors, Phagescript vectors, pNH8A, pNH16a, pNH18A, pNH46A, ptrc99a, pKK223-3, pKK233-3, pDR540, pRIT5. Among preferred eukaryotic vectors are pFastBacl pWINEO, pSV2CAT, pOG44, pXTl and pSG, pSVK3, pBPV, pMSG, and pSVL. Other suitable vectors will be readily apparent to the skilled artisan.

Recombinant constructs can be prepared and used to transfect, can express viral proteins, including those described herein, into eukaryotic cells and/or prokaryotic cells. Thus, the invention provides for host cells which comprise a vector (or vectors) that contain nucleic acids which encode alphavirus structural proteins, including capsid, E3, E2, 6K, and E1 or portions thereof, and a vector that comprises nucleic acids which encode alphavirus nsp1, nsp2, nsp3 and nsp4, and at least one of gene of interest under conditions which allow the formation of ARPs.

In one embodiment, said vector is a recombinant baculovirus. In another embodiment, said recombinant baculovirus is transfected into an insect cell. In a preferred embodiment, said cell is an insect cell. In another embodiment, said insect cell is a Sf9 cell.

One particular bacterial expression system for polypeptide production is the *E. coli* pET expression system (Novagen®, Inc., Madison, Wis). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, a recombinant polypeptide is then isolated according to standard methods known in the art, for example, those described herein.

Another bacterial expression system for polypeptide production is the pGEX expression system (Pharmacia™). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Depending on the vectors and host cells selected, the ARPs are produced by growing host cells transfected by the vectors under conditions whereby the recombinant proteins are expressed and the alphavirus replicon is generated, and ARPs containing alphavirus replicon being packaged with the particle of alphavirus structural proteins are formed. In one embodiment, the invention comprises a method of producing an ARP, that involves co-transfecting a vector comprising a polynucleotide encoding alphavirus non-structural protein nsp1, nsp2, nsp3 and nsp4, and at least one gene of interest, at least one vectors each encoding at least one alphavirus protein into suitable host cells and expressing said alphavirus protein under conditions that allow ARP formation. In another embodiment, the eukaryotic cell is selected from the group consisting of, yeast, insect, amphibian, avian or mammalian cells. The selection of the appropriate growth conditions is within the skill or a person with skill of one of ordinary skill in the art.

Methods to grow cells that produce ARPs of the invention include, but are not limited to, batch, batch-fed, continuous and perfusion cell culture techniques. In one embodiment, cells co-transfected with a vector encoding an alphavirus replicon and a vector comprising a polypeptide encoding capsid, and a vector comprising a polynucleotide encoding envelope proteins, such as those derived from a CHIKV or VEEV are grown in a bioreactor or fermentation chamber where cells propagate and express protein (e.g., recombinant proteins) for purification and isolation. Typically, cell culture is performed under sterile, controlled temperature and atmospheric conditions. A bioreactor is a chamber used to culture cells in which environmental conditions such as temperature, atmosphere, agitation and/or pH can be monitored. In one embodiment, the bioreactor is a stainless steel chamber. In another embodiment, said bioreactor is a pre-sterilized plastic bag (e.g., Cellbag®, Wave Biotech, Bridgewater, N.J.). In other embodiment, said pre-sterilized plastic bags are about 50 L to 1000 L bags.

The ARPs are isolated using methods that preserve the integrity thereof, such as by gradient centrifugation, e.g., cesium chloride, sucrose and iodixanol, as well as standard purification techniques including, e.g., ion exchange and gel filtration chromatography.

The following is an example of how ARPs of the invention can be made, isolated and purified. A person of skill in the art appreciates that there are additional methods that can be used to make and purify ARPs. Accordingly, the invention is not limited to the methods described herein.

In general, production of ARPs of the invention is accomplished by seeding a mammalian cell (e.g., human embryonic kidney (293T) cells) or Sf9 cells (non-infected) into shaker flasks, allowing the cells to expand and scaling up as the cells grow and multiply (for example from a 125-ml flask to a 50 L Wave bag). The medium used to grow the cells is formulated for the appropriate cell line (preferably serum free media, e.g., insect medium ExCell-420, JRH). Next, the cells are transfected or infected with an appropriate vector (e.g., mammalian expression vector or for SF (cells recombinant baculovirus at the most efficient multiplicity of infection (e.g., from about 1 to about 3 plaque forming units per cell). The polynucleotides, or portions thereof, are expressed in the cells where they self-assemble into ARPs and are secreted from the cells approximately 24 to 72 hours post infection (hpi). Usually, transfection or infection is most efficient when the cells are in mid-log phase of growth ($4$-$8.\times10<6>$ cells/ml) and are at least about 90% viable. Additionally, the transfected cells may be exposed to high pH conditions in cell culture (pH >7.2, e.g., pH 7.2, 7.3, 7.4, 7.5, 7.6, 7.7, 7.8, 7.9, 8.0, 8.1, 8.2, 8.3, 8.4, 8.5, 8.6, 8.7, 8.8, or higher) to increase ARP production.

ARPs of the invention are harvested approximately 48 to 120 hours post infection, when the levels of ARPs in the cell culture medium are near the maximum but before extensive cell lysis. The cell density and viability at the time of harvest can be about $0.5\times10^6$ cells/ml to about $1.5\times10^6$ cells/ml with at least 20% viability, as shown by dye exclusion assay. Next, the medium is removed and clarified. NaCl can be added to the medium to a concentration of about 0.4 to about 1.0 M, preferably to about 0.5 M, to avoid ARP aggregation. The removal of cell and cellular debris from the cell culture medium containing ARPs of the invention can be accomplished by tangential flow filtration (TFF) with a single use, pre-sterilized hollow fiber 0.5 or $1.00\mu\pi i$ filter cartridge or a similar device.

Additionally, the ARPs may be exposed to high pH conditions during purification (pH >7.2, e.g., pH 7.2, 7.3, 7.4, 7.5, 7.6, 7.7, 7.8, 7.9, 8.0, 8.1, 8.2, 8.3, 8.4, 8.5, 8.6, 8.7, 8.8, or higher) to increase ARP production.

Next, ARPs in the clarified culture medium are concentrated by ultrafiltration using a disposable, pre-sterilized 500,000 molecular weight cut off hollow fiber cartridge. The concentrated ARPs can be diafiltrated against 10 volumes pH 7.0 to 8.0 phosphate-buffered saline (PBS) containing 0.5 M NaCl to remove residual medium components.

The concentrated, diafiltered ARPs can be furthered purified on a 20% to 60% discontinuous sucrose gradient in pH 7.2 PBS buffer with 0.5 M NaCl by centrifugation at 6, 500× g for 18 hours at about 4 C to about 10 C. Usually ARPs will form a distinctive visible band between about 30% to about 40% sucrose or at the interface (in a 20% and 60% step gradient) that can be collected from the gradient and stored. This product can be diluted to comprise 200 mM of NaCl in preparation for the next step in the purification process. This product contains ARPs and may contain intact baculo virus particles.

Further purification of ARPs can be achieved by anion exchange chromatography, or 44% isopycnic sucrose cushion centrifugation. In anion exchange chromatography, the sample from the sucrose gradient (see above) is loaded into column containing a medium with an anion (e.g., Matrix Fractogel® EMD TMAE) and eluded via a salt gradient (from about 0.2 M to about 1.0 M of NaCl) that can separate the ARP from other contaminates (e.g., baculovirus and DNA/RNA). In the sucrose cushion method, the sample comprising the ARPs is added to a 44% sucrose cushion and centrifuged for about 18 hours at 30,000 g. ARPs form a band at the top of 44% sucrose, while baculovirus precipitates at the bottom and other contaminating proteins stay in the 0% sucrose layer at the top. The ARP peak or band is collected.

The intact baculovirus can be inactivated, if desired. Inactivation can be accomplished by chemical methods, for example, formalin or .beta.-propiolactone (BPL). Removal and/or inactivation of intact baculovirus can also be largely accomplished by selective using precipitation and chromatographic methods known in the art, as exemplified above. Methods of inactivation comprise incubating the sample containing the ARPs in 0.2% of BPL for 3 hours at about 25° C. to about 27° C. The baculovirus can also be inactivated by incubating the sample containing the ARPs at 0.05% BPL at 4° C. for 3 days, then at 37° C. for one hour.

After the inactivation/removal step, the product comprising ARPs can be run through another diafiltration step to remove any reagent from the inactivation step and/or any residual sucrose, and to place the ARPs into the desired buffer (e.g., PBS). The solution comprising ARPs can be sterilized by methods known in the art (e.g., sterile filtration) and stored in the refrigerator or freezer.

The above techniques can be practiced across a variety of scales. For example, T-flasks, shake-flasks, spinner bottles, up to industrial sized bioreactors. The bioreactors can comprise either a stainless steel tank or a pre-sterilized plastic bag (for example, the system sold by Wave Biotech, Bridgewater, N.J.). A person with skill in the art will know what is most desirable for their purposes.

As described herein, upon administration to a desired host, the ARPs of the present invention are taken up by cells normally infected by the alphavirus from which the structural proteins are derived. The gene of interest contained in the replicon is internalized into the cell upon ARP entry. This property facilitates the use of the ARPs described herein as delivery vehicles of the gene because they enable the delivery of the gene of interest into a desired cell.

Whereas natural alphavirus genomes encode virus structural proteins in addition to the non-structural replicase polyprotein, the alphavirus replicon does not encode alphavirus structural proteins. Thus the alphavirus replicon can lead to the production of genomic RNA copies of itself in a cell, but not to the production of RNA-containing virions. The inability to produce these virions means that, unlike a wild-type alphavirus, the replicon cannot perpetuate itself in infectious form. The alphavirus structural proteins which are necessary for perpetuation in wild-type viruses are absent from the replicon and their place is taken by at least one gene of interest, such that the subgenomic transcript encodes the protein of interest rather than the structural alphavirus structural proteins.

Thus, in certain embodiments, the ARP comprises a gene of interest that may be, or may encode, such as a therapeutic or diagnostic agent(s) that needs to be delivered to a subject, e.g., imaging agent, nucleic acid sequence (including siRNA and microRNA), radionuclide, hormone, peptide, antiviral agent, antitumor/chemotherapeutic agent, cell growth modulating agent, cell growth inhibitor, cytokine, antigen, adjuvant and toxin. The replicon packaged in the particle of the virus structural proteins should not adversely affect the stability of the ARP. This may be determined by producing ARP containing a given gene of interest and assessing its effects, if any, on ARP stability.

Accordingly, the present invention provides methods for introducing a gene of interest into a cell. According to the present invention, the gene of interest is contained in the alphavirus replicon and alphavirus replicon is packaged with the particle of alphavirus structural proteins. In related embodiments, the ARP is contacted with a cell. In related embodiments, the ARP is allowed to enter the cell, thereby resulting in delivery of the gene of interest into the cell.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The gene of interest may be a gene that encodes an antigen. ARPs of the present invention may be prepared in an injectable form, either as a liquid solution or as a suspension. Solid forms suitable for injection may also be prepared as emulsions, or with the ARPs encapsulated in liposomes. Vaccine antigens are usually combined with a pharmaceutically acceptable carrier, which includes any carrier that does not induce the production of antibodies harmful to the subject receiving the carrier. Suitable carriers typically comprise large macromolecules that are slowly metabolized, such as proteins, polysaccharides, polylactic acids, polyglycolic acids, polymeric amino acids, amino acid copolymers, lipid aggregates, and inactive virus particles. Such carriers are well known to those skilled in the art. These carriers may also function as adjuvants.

The ARPs described herein may be administered in combination with an adjuvant (e.g., Ribi). Adjuvants are immunostimulating agents that enhance vaccine effectiveness. If desired, the ARP comprising one or more alphavirus polypeptides or fragments or variants thereof are administered in combination with an adjuvant that enhances the effectiveness of the immune response generated against the antigen of interest. Effective adjuvants include, but are not limited to, aluminum salts such as aluminum hydroxide and aluminum phosphate, muramyl peptides, bacterial cell wall components, saponin adjuvants, and other substances that act as immunostimulating agents to enhance the effectiveness of the composition.

Immunogenic compositions, i.e., the ARPs described herein, pharmaceutically acceptable carrier and adjuvant, also typically contain diluents, such as water, saline, glycerol, ethanol. Auxiliary substances may also be present, such as wetting or emulsifying agents, pH buffering substances, and the like. Proteins may be formulated into the vaccine as neutral or salt forms. The immunogenic compositions are typically administered parenterally, by injection; such injection may be either subcutaneously or intramuscularly. Additional formulations are suitable for other forms of administration, such as by suppository or orally. Oral compositions may be administered as a solution, suspension, tablet, pill, capsule, or sustained release formulation.

Immunogenic compositions are administered in a manner compatible with the dose formulation. The immunogenic composition comprises an immunologically effective amount of the ARP described herein and other previously mentioned components. By an immunologically effective amount is meant a single dose, or a composition administered in a multiple dose schedule, that is effective for the treatment or prevention of an infection. The dose administered will vary, depending on the subject to be treated, the subject's health and physical condition, the capacity of the subject's immune system to produce antibodies, the degree of protection desired, and other relevant factors. Precise amounts of the active ingredient required will depend on the judgement of the practitioner, but typically range between 5 µg to 250 µg of antigen per dose.

Pharmaceutical Compositions and Administration

The invention features pharmaceutical compositions that comprise ARPs as described herein. The pharmaceutical compositions useful herein contain a pharmaceutically acceptable carrier, including any suitable excipient, diluent or which includes any pharmaceutical agent that does not itself induce the production of an immune response harmful to the vertebrate receiving the composition, and which may be administered without undue toxicity and a ARP of the invention. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. These compositions can be useful as a vaccine and/or antigenic compositions for inducing a protective immune response in a vertebrate.

Pharmaceutically acceptable carriers include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation should suit the mode of administration. In a preferred embodiment, the formulation is suitable for administration to humans, preferably is sterile, non-particulate and/or non-pyrogenic.

The composition, if desired, can also contain minor amounts of wetting or emulsifying agents, or pH buffering agents. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

In certain embodiments, the ARP composition is supplied in liquid form, for example in a sealed container indicating the quantity and concentration of the ARP composition.

Preferably, the liquid form of the ARP composition is supplied in a hermetically sealed container at least about 50 µg/ml, more preferably at least about 100 µg/ml, at least about 200 µg/ml, at least 500 µg/ml, or at least 1 mg/ml.

Alternatively, the vaccine formulation is administered intranasally, either by drops, large particle aerosol (greater than about 10 microns), or spray into the upper respiratory tract or small particle aerosol (less than 10 microns) or spray into the lower respiratory tract. While any of the above routes of delivery results in an immune response, intranasal administration confers the added benefit of eliciting mucosal immunity at the site of entry of many viruses, including alphaviruses, for example CHIKV or VEEV.

Thus, the invention also comprises a method of formulating a vaccine or antigenic composition that induces immunity to an infection or at least one symptom thereof to a mammal, comprising adding to said formulation an effective dose of ARPs, e.g., alphavirus (e.g., CHIKV or VEEV).

In certain cases, stimulation of immunity with a single dose is preferred, however additional dosages can be also be administered, by the same or different route, to achieve the desired effect. In neonates and infants, for example, multiple administrations may be required to elicit sufficient levels of immunity. Administration can continue at intervals throughout childhood, as necessary to maintain sufficient levels or protection.

Similarly, adults who are particularly susceptible to repeated or serious infections, such as, for example, health care workers, day care workers, family members of young children, the elderly, and individuals with compromised cardiopulmonary function or immune systems may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

The dosage of the pharmaceutical formulation can be determined readily by the skilled artisan, for example, by first identifying doses effective to elicit a prophylactic or therapeutic immune response, e.g., by measuring the serum titer of virus specific immunoglobulins or by measuring the inhibitory ratio of antibodies in serum samples, or urine samples, or mucosal secretions. Said dosages can be determined from animal studies. A non-limiting list of animals used to study the efficacy of vaccines include the guinea pig, hamster, ferrets, chinchilla, mouse and cotton rat, and non-human primates. Most animals are not natural hosts to infectious agents but can still serve in studies of various aspects of the disease. For example, any of the above animals can be dosed with a vaccine candidate, e.g., ARPs of the invention, to partially characterize the immune response induced, and/or to determine if any neutralizing antibodies have been produced. For example, many studies have been conducted in the mouse model because mice are small size and their low cost allows researchers to conduct studies on a larger scale.

In addition, human clinical studies can be performed to determine the preferred effective dose for humans by a skilled artisan. Such clinical studies are routine and well known in the art. The precise dose to be employed will also depend on the route of administration. Effective doses may be extrapolated from dose-response curves derived from in vitro or animal test systems.

As also well known in the art, the immunogenicity of a particular composition can be enhanced by the use of non-specific stimulators of the immune response, known as adjuvants. Adjuvants have been used experimentally to promote a generalized increase in immunity against unknown antigens. Immunization protocols have used adjuvants to stimulate responses for many years, and as such, adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. The inclusion of any adjuvant described in Vogel et al., "A Compendium of Vaccine Adjuvants and Excipients (2nd Edition)," herein incorporated by reference in its entirety for all purposes, is envisioned within the scope of this invention.

Exemplary adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween®-80 emulsion also is contemplated. MF-59, Novasomes®, MHC antigens may also be used.

The ARPs of the invention can also be formulated with "immune stimulators." These are the body's own chemical messengers (cytokines) to increase the immune system's response. Immune stimulators include, but not limited to, various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the ARPs, or can be administered separately. Either the protein or an expression vector encoding the protein can be administered to produce an immunostimulatory effect. Thus in one embodiment, the invention comprises antigenic and vaccine formulations comprising an adjuvant and/or an immune stimulator.

According to the invention, the delivery system comprising said ARP can deliver a gene of interest into the cytoplasm of eukaryotic cells, thereby can treat cancers, viral infections, neurological disorders, autoimmune diseases, graft rejection and monogenic or polygenic hereditary diseases.

The invention will be described in detail with reference to the following examples, which, however, are not intended to limit the scope of the present application.

Example 1

Figure 2:
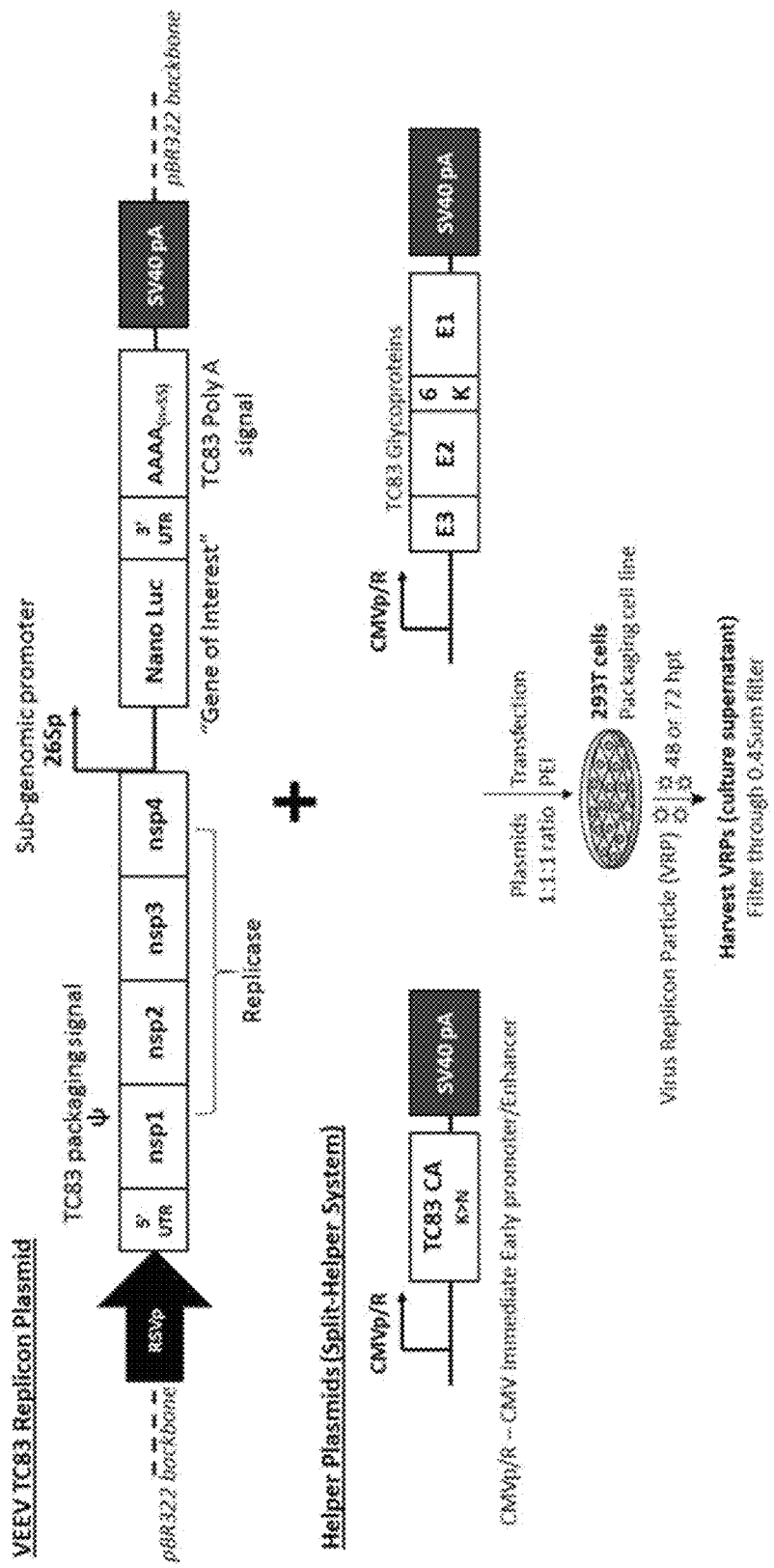
FIG. 2 shows the construction of the VEEV replicon particle.

Construction of VEEV Replicon Particles (VRPs) Schematic procedure is shown in FIG. 2.

Establishment of VEEV Replicon Plasmid Expressing Luciferase

1) Full-length VEEV TC83 non-structural protein(nsp)1, nsp2, nsp3 and nsp4 fragment was synthesized (ThermoFisher). Similarly, gblocks corresponding to various fragments of the Replicon construct were synthesized (IDT) as follows—

2) VEEV gblock1—ClaI-RSVp-5' UTR-nsp1 (bp1-470)-RsrII-ApaI-26Sp-sgRNA up to ATG of the VEEV CA gene. This fragment had a 36 bp overlap with the pBR322 backbone plasmid at the 5' end. This is fragment #1.

3) VEEV gblock2—This fragment had a 64 bp overlap with VEEV gblock1 starting at the ApaI site up to the ATG start codon. This was followed by the NanoLuc® ORF (Promega®) and the first 72 bases of the VEEV 3' UTR.

4) Cloning of fragment #2-VEEV gblock2, full-length VEEV 3' UTR and the VEEV PolyA signal (A (n=55)) were first assembled by overlap extension PCR using the oligomers shown in the table below:

TABLE 1

| Primer Name | Sequence 5' → 3' |
|---|---|
| VEEV_gblock2_fwd | tcattcagctacctgagaggg (SEQ ID NO: 7) |
| VEEV_gblock2_rev | aaataaaaattttaaggcggcatgc (SEQ ID NO: 8) |
| VEEV_Oligo1_fwd | ttaaaattttattttattttctttttctttt ccgaatcggattttgttttaatatttc (SEQ ID NO: 9) |
| VEEV_Oligo2_rev | CATCAATGTATCTTATCATGTCTGtcgcgaTT TTTTTTTTTTTTTTTTTTTTTTTTTTTTTT TTTTTTTTTTTTTTTTTTTTgaaatattaaa aaca (SEQ ID NO: 10) |

VEEV_Oligo2 has a 15 bp overlap with the pBR322 backbone plasmid.

5) Next, the VEEV gblock1 (fragment #1), fragment #2 and pBR322 backbone (digested with ClaI and NruI-HF) were assembled using Gibson Assembly to obtain the pBR322-RSVp-RsrII-ApaI-26Sp-sgRNA-NanoLuc-A (n=55)-SV40 pA backbone construct (BB). This backbone construct lacked the full-length TC83 nsp1-4 fragment.

Figure 3:
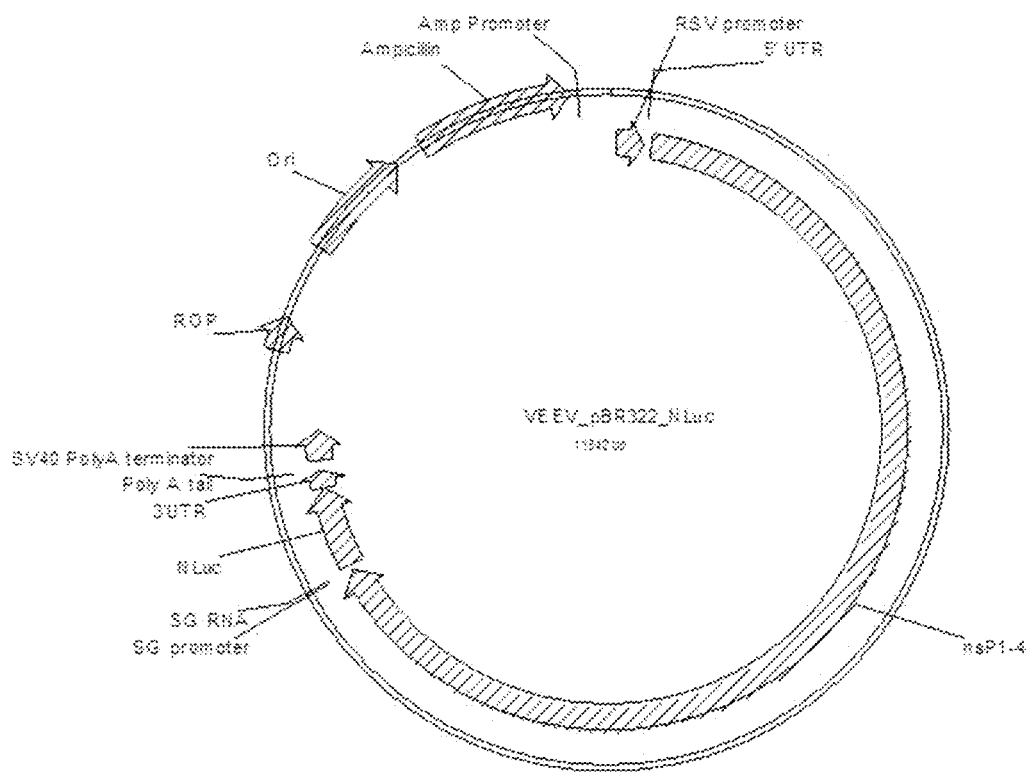
FIG. 3 shows VEEV_pBR322_NLuc vector.

6) The nsp1-4 fragment (bp 470-7461) was amplified from the synthesized Thermo plasmid obtained in 1) using primers containing the RsrII and ApaI restriction sites—
i) 5'-ccggccCGGACCGacaagtctctatcacc-3' (SEQ ID NO: 11, fwd primer) and ii) 5'-ggccggGGGCCCctctcaggtagctgaatg-3' (SEQ ID NO: 12, rev primer). This PCR amplified nsp fragment was cloned into the BB backbone plasmid using the RsrII and ApaI sites to obtain the full-length VEEV TC83 Replicon construct. (FIG. 3)

Helper Plasmids

Figure 4:
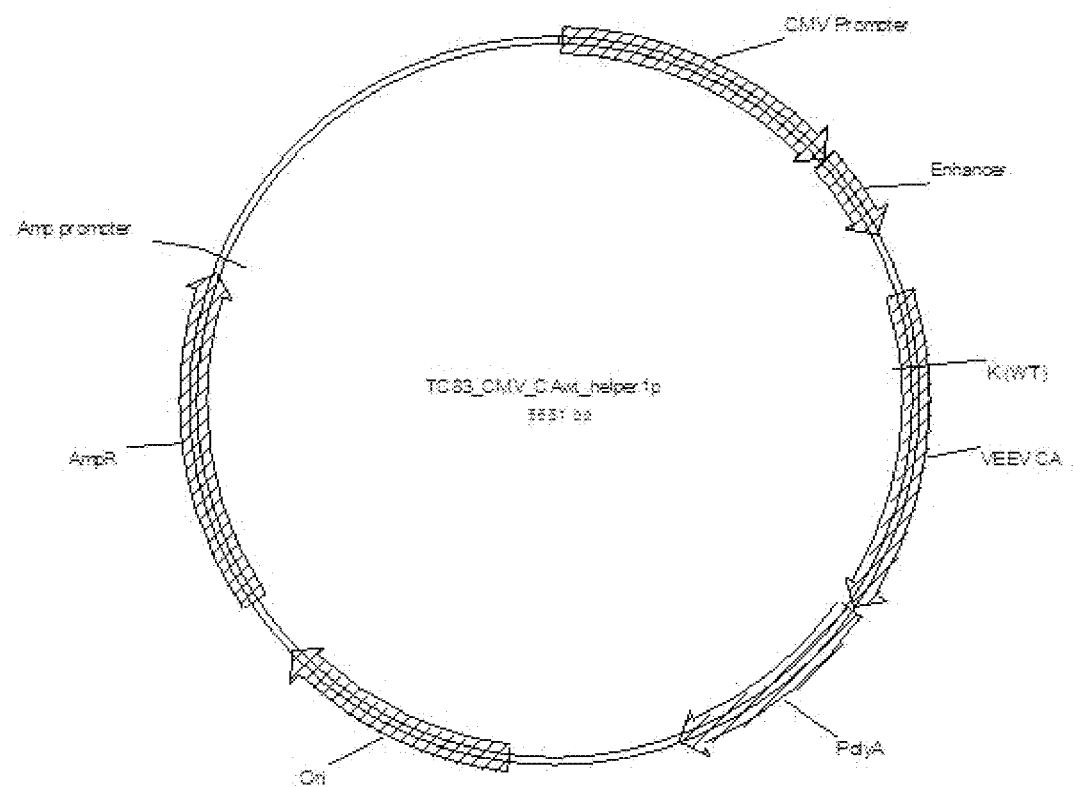
FIG. 4 shows TC83_CMV_CAwt_helper 1p vector.
Figure 5:
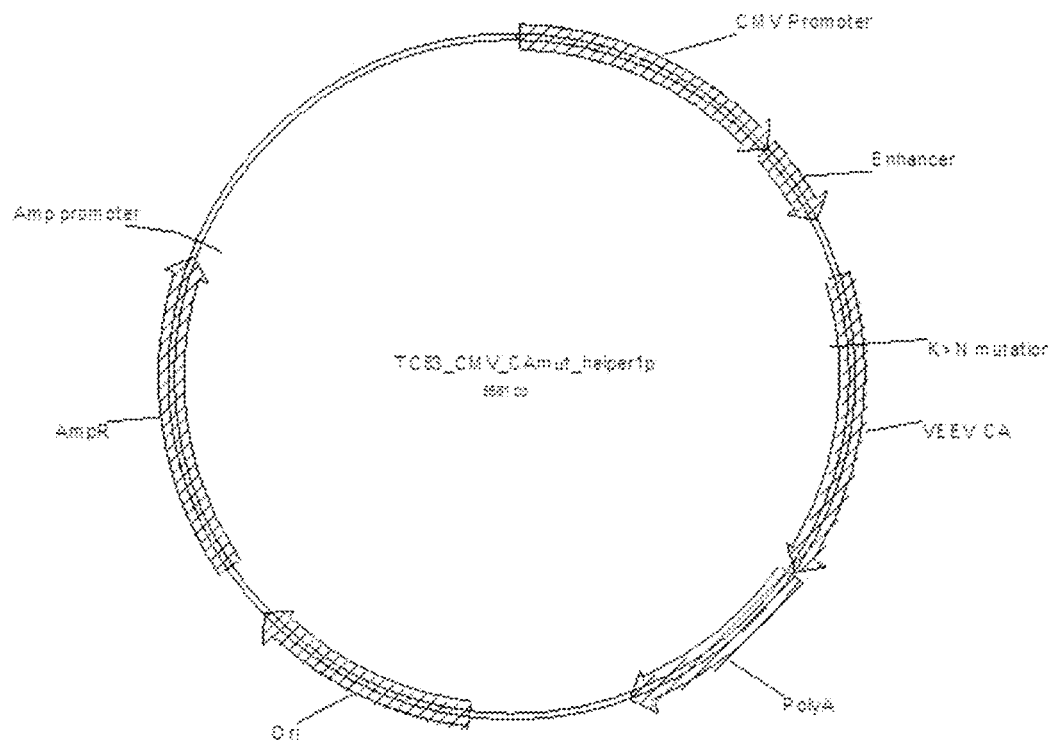
FIG. 5 shows TC83_CMV_CAmut_helper 1P vector.

Helper plasmid constructs encoding the VEEV TC83 capsid are shown in FIGS. 4 and 5. The constructs express wild type VEEV capsid protein (SEQ ID NO: 1) and VEEV Capsid having a mutation in the NLS (K64N, SEQ ID NO: 2), respectively.

Figure 6:
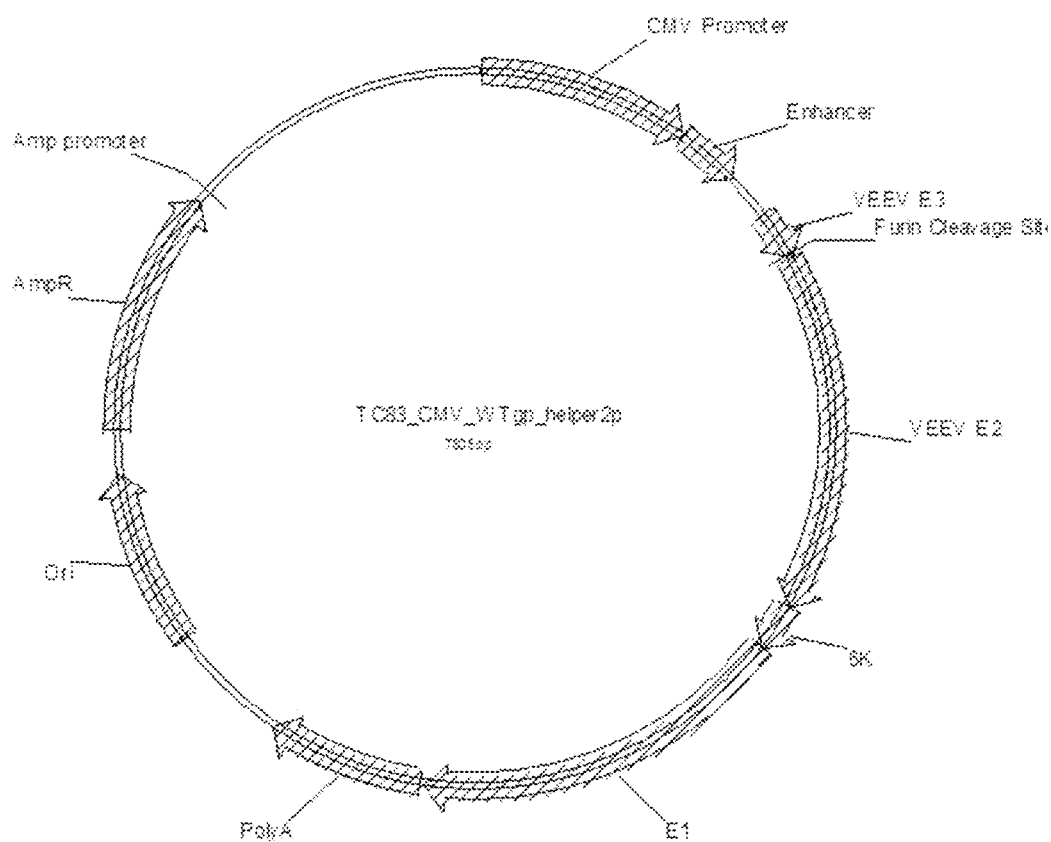
FIG. 6 shows TC83_CMV_WTgp_helper 2P vector
Figure 7:
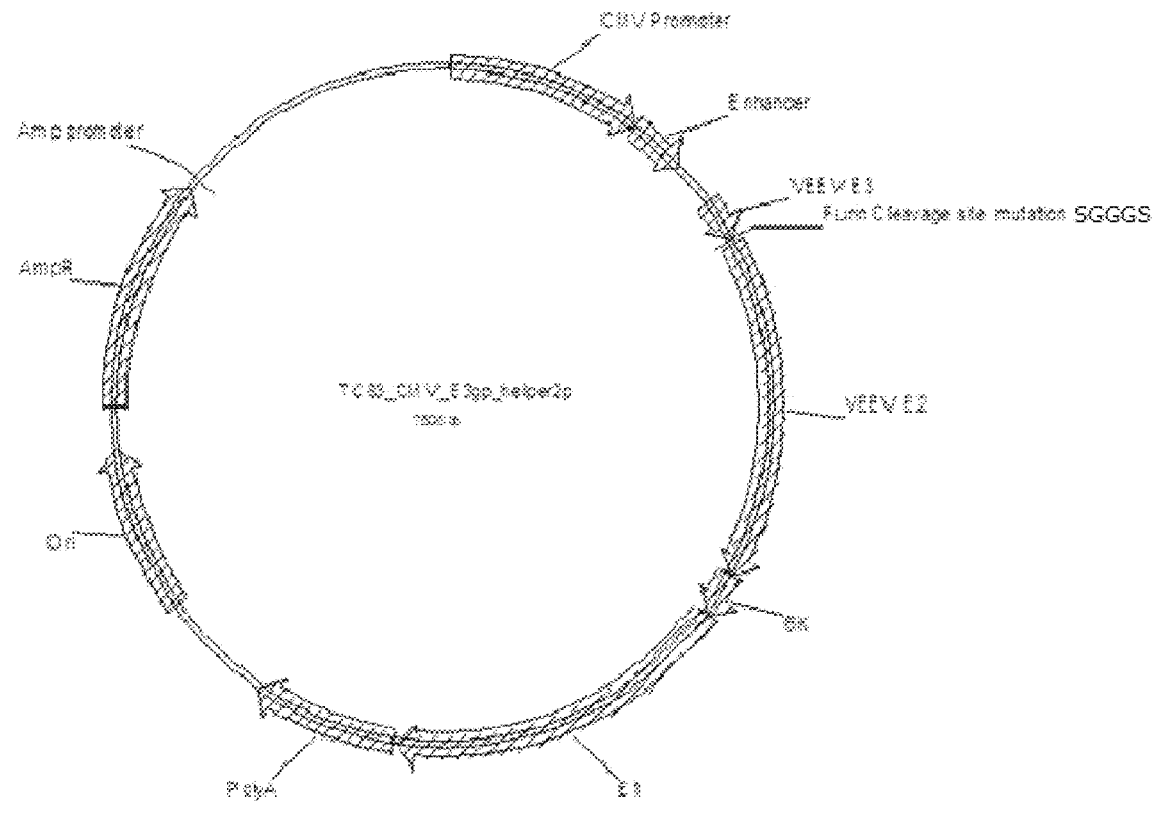

Helper plasmid constructs expressing the VEEV TC83 glycoproteins E3-E2-6K-E1 used herein are shown in FIGS. 6 and 7. The constructs express wild type VEEV TC83 glycoproteins E3-E2-6K-E1 (SEQ ID NO: 3) and E3 modified E3-E2-6K-E1 (furin site at the end of E3 RKRR (SEQ ID NO: 16) was replaced with SGGGS (SEQ ID NO: 15), SEQ ID NO: 4), respectively.

Cell Culture and Co-Transfection 293T cells were seeded in a 6-well plate in complete DMEM containing 10% FBS, Penicillin and Streptomycin. The cells were co-transfected with equal amounts of the VEEV RSVp-NLuc construct containing (VR) (SEQ ID NO: 5) or lacking (BB) the nsp1-4 fragment, along with helper plasmid encoding capsid and that encoding glycoproteins E1-6K-E2-E3 using PEI (1.7 μg of each plasmid). The combination of the helper plasmids was (SEQ ID NO: 1 and 3), (SEQ ID NO: 1 and 4), (SEQ ID NO: 2 and 3) or (SEQ ID NO: 2 and 4). Cells were incubated with the transfection mixture for about 3 hours at 37° C., following which the transfection mixture was removed, cells were washed with 1×PBS and fresh DMEM was added. The packaged Virus Replicon Particles (VRPs) were harvested either 48 hpt (hours post transfection) or 72 hpt. To harvest the VRPs, the culture supernatant of the transfected cells was obtained by centrifuging the cell culture at 1200 rpm for 5 min at 4° C. to pellet any cell debris. The supernatant was filtered through a 0.45 μm filter. The harvested VRPs were either stored at 4° C. or −80° C.

Example 2

Figure 8:
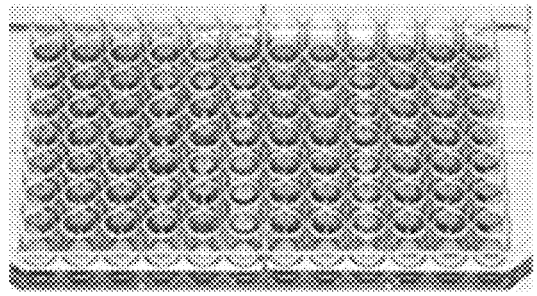
FIG. 8 shows schematic protocol for determining the packaging ability of VEEV replicon into VEE VRPs.

Determining the Packaging Ability of the VEEV Replicon into VEE Virus Replicon Particles (VRPs)
Infection and Luciferase Assay Schematic protocol is shown in the FIG. 8.

293T cells were seeded in complete DMEM in a 96-well plate at a density of approximately 10,000 cells per well. Cells were infected with undiluted or 2-fold serial dilutions of the harvested VRPs at 37° C. At 14 hours post infection (hpi), the VRPs were removed; the cells were washed with PBS and fresh DMEM was added to the wells. Cells were further incubated and harvested for Luciferase assay at 24, 48, and 72 hpi. Luciferase assay was performed by adding equal amounts of infected cells and Nano-Glo® Luciferase Assay System (Promega®) to a white bottom opaque 96-well plate (Costar). Luciferase activity was measured immediately using the Bio-Tek Synergy HTX microplate reader.

Result

Figure 9:
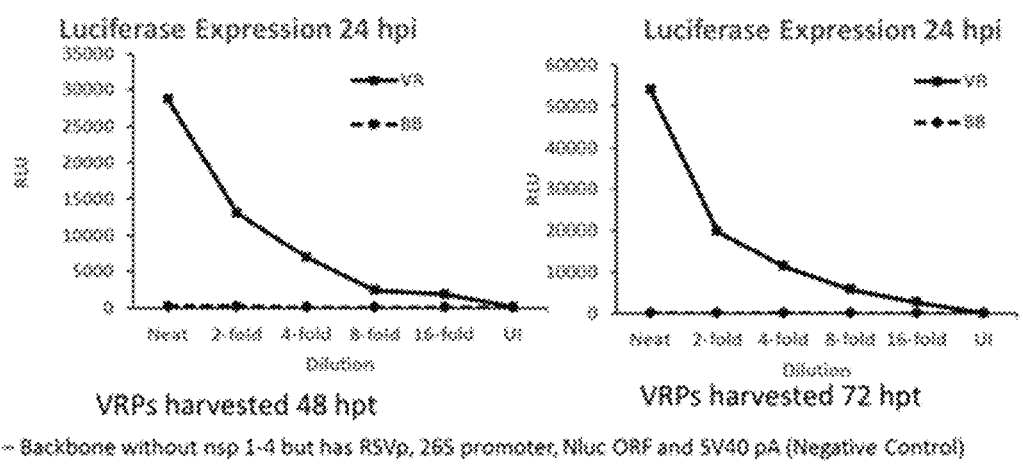
FIG. 9 shows results of the test shown in FIG. 8.

Results are shown in FIG. 9. Luciferase expression was confirmed in the cells infected with the VRPs (VR) as early as 24 hpi. Cells infected with the backbone construct lacking nsp 1-4 (BB) expressed almost no luciferase.

Example 3

New VEEV Replicon Constructs

Figure 10:
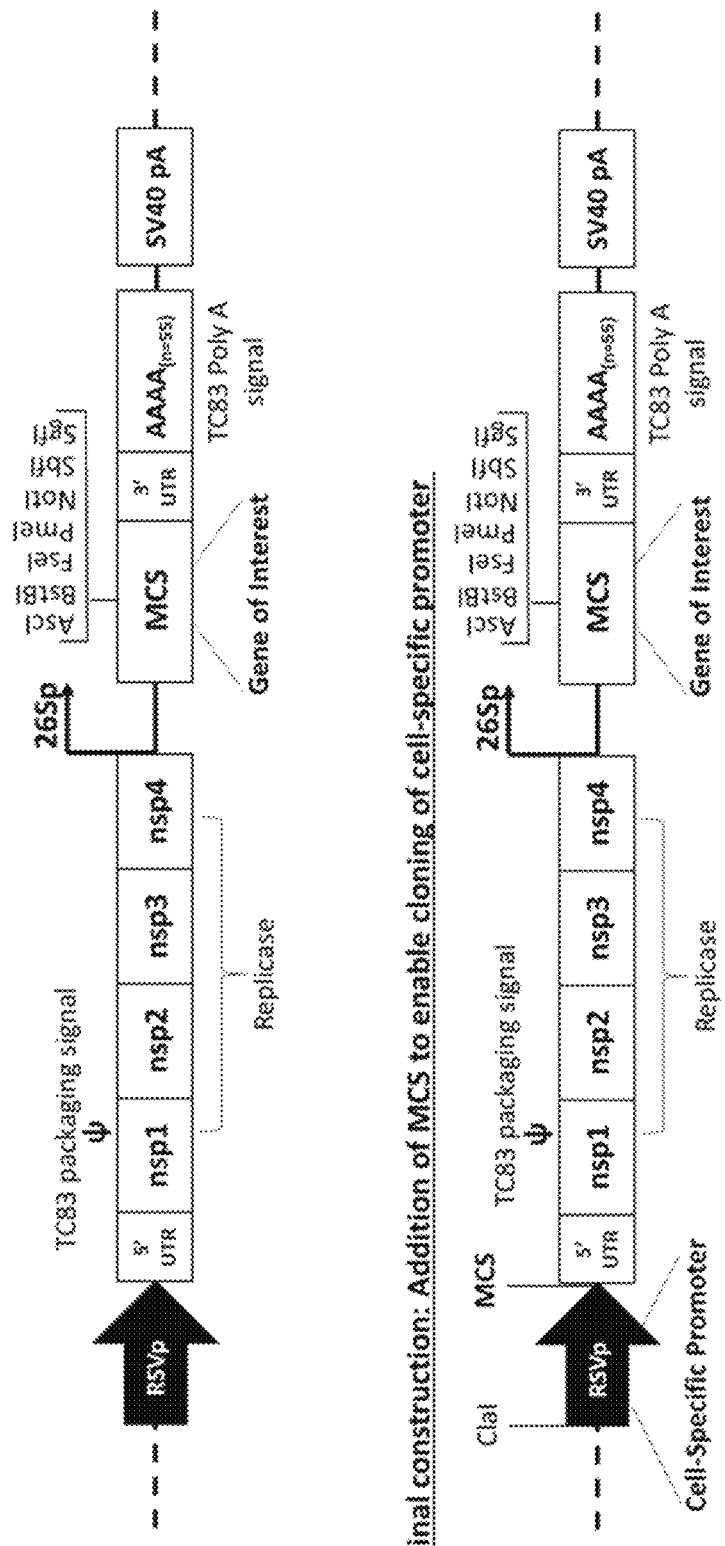
FIG. 10 shows incorporation of multiple cloning site in the construction of the VEEV replicon particle.
Figures 11, 12:
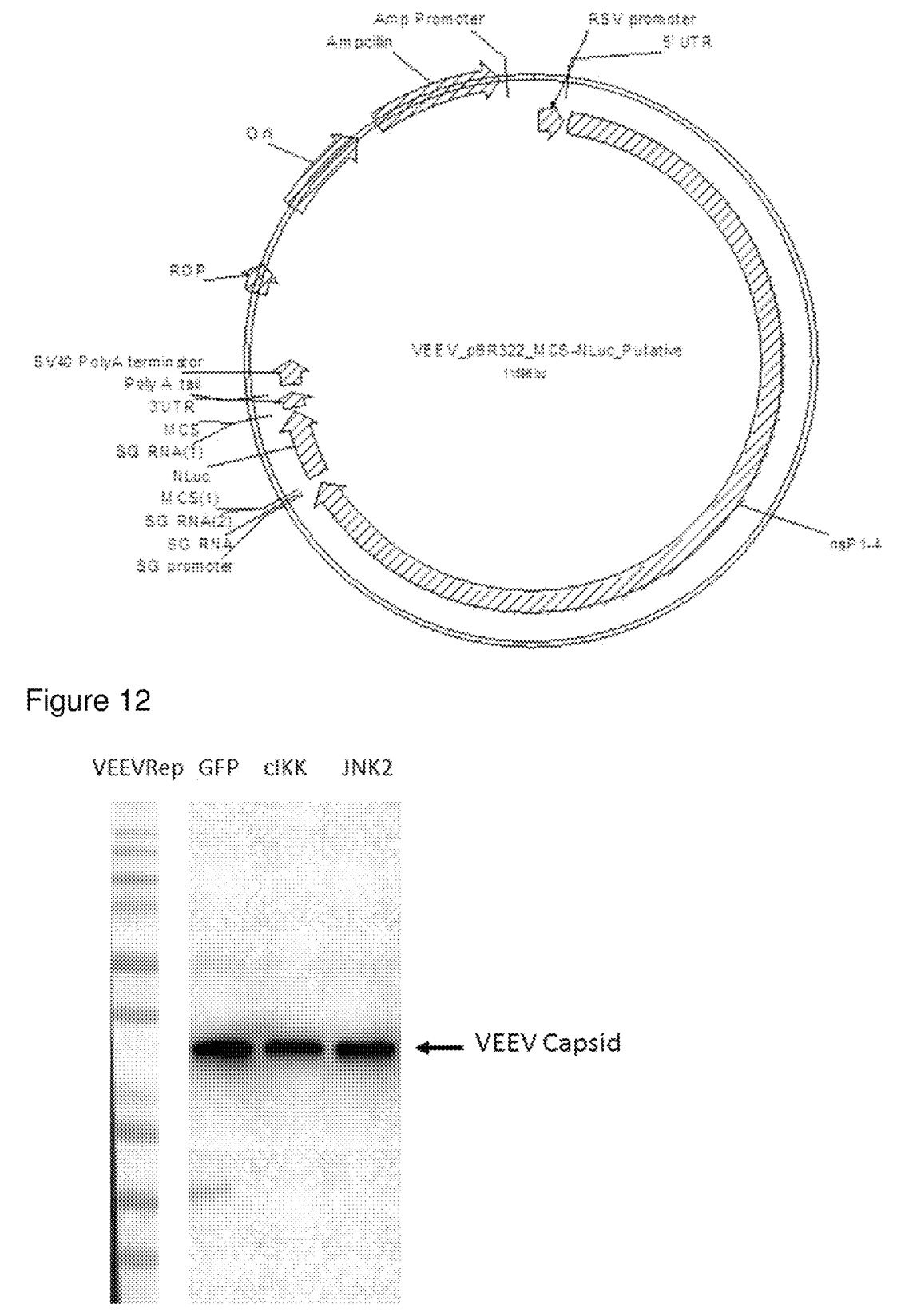

New VEEV TC83 replicon plasmid constructs was prepared by introducing multiple cloning site (MCS) to enable introducing various "gene of interest". The schematic protocol is shown in FIG. 10. The construct is shown in FIG. 11 and SEQ ID NO: 6. In the construct of FIG. 11, a nucleotide encoding luciferase is introduced as gene of interest. Promoter in the plasmid may be selected in view of the cells to be infected.

Example 4

Preparation of VRPs with/without a mutation in Capsid and/or E3-E2-6K-E1, and having a gene of interest In this example, VEEV replicon plasmid containing a gene of interest was co-transfected with VEEV Capsid helper plasmid and VEEV E3-E2-6K-E1 glycoprotein helper plasmid to 293T cells in the similar manner as Example 1. As the gene of interest, genes encoding luciferase, GFP, IKK or JNK2 was employed.

The following plasmids were used:
  i-1) plasmid comprising a polynucleotide encoding VEEV CT83 wild type capsid protein, or
  i-2) plasmid comprising a polynucleotide encoding VEEV CT83 capsid protein having a mutation in the NLS (K64N).
  ii-1) plasmid comprising a polynucleotide encoding wild type VEEV CT83 E3-E2-6K-E1, or
  ii-2) plasmid comprising a polynucleotide encoding VEEV CT83 E3-E2-6K-E1, having mutation in the furin site in E3 and
  iii) plasmid comprising polynucleotide encoding VEEV CT83 nsp1, nsp2, nsp3 and nsp4, and a gene of interest encoding luciferase, GFP, IKK or JNK2.

Co-Transfection 293T cells were co-transfected with the VEEV TC83 replicon plasmid comprising the gene of interest, a helper plasmid encoding VEEV capsid (WT or mutation) and a helper plasmid encoding E3-E2-6K-E1 (WT or mutation). Three plasmids (1 μg of capsid, 1 μg of E3-E2-6K-E1 and 10 μg of VEEV replicon containing the gene of interest) were transfected to 293T cells (by PEI method) and cells were incubated 4-7 days. Then, VRPs were harvested from the supernatant and purified by optiprep density sedimentation.

The purified VRPs were confirmed by western blotting using anti-VEEV antibody (ATCC) as the first antibody (1:2000) and anti-mouse IgG (1:4000) as the secondary antibody. The results of VRPs obtained by using the following plasmids are shown in FIG. 12:
  i) plasmid comprising a polynucleotide encoding VEEV CT83 capsid protein having a mutation in the NLS (K64N).
  ii) plasmid comprising a polynucleotide encoding wild type VEEV CT83 E3-E2-6K-E1, and
  iii) plasmid comprising polynucleotide encoding VEEV CT83 nsp1, nsp2, nsp3 and nsp4, and also a polynucleotide encoding GFP, IKK or JNK2.

Example 5

VRPs obtained in Example 4 using the following vectors were used:
  i) plasmid comprising a polynucleotide encoding VEEV CT83 capsid protein having a mutation in the NLS (K64N).
  ii) plasmid comprising a polynucleotide encoding wild type VEEV CT83 E3-E2-6K-E1, and
  iii) plasmid comprising polynucleotide encoding VEEV CT83 nsp1, nsp2, nsp3 and nsp4, and also a polynucleotide encoding IKK or JNK2.

293T Cells were infected with the VRPs that contain IKK or JNK2 gene. The infection of VRPs to 293T cells was conducted in the same manner as Example 2.

The expression of IKK in the VRP-infected 293T cells was confirmed by western blotting. As positive control, 293T cells transfected with IKK expression vector plasmid were used. Cell lysate was subjected to western blotting with Rb anti-IKK antibody (Proteintech) as the first antibody (1:500) and HRP labelled anti-RbIgG as the secondary antibody (1:4000).

Figure 13:
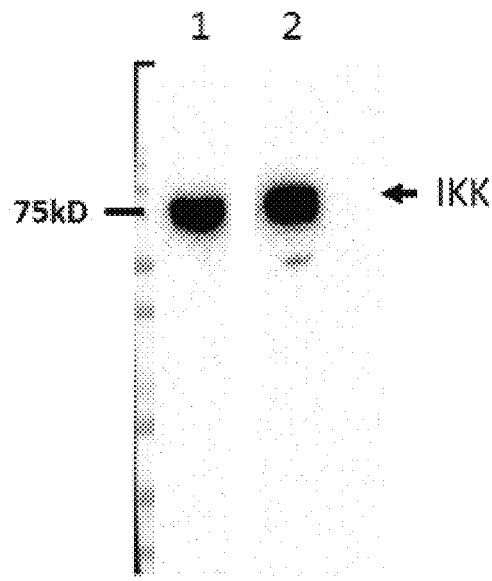
FIG. 13 shows western blotting of the cells infected by VRPs comprising a nucleotide encoding IKK. Lane 1, cells infected by VRPs, Lane 2, cells transfected by IKK plasmid vector (positive control).

Results are shown in FIG. 13. In FIG. 13, Lane 1 shows 293T cells infected with the VRPs. Lane 2 shows positive control, i.e. cells transfected with IKK expression vector plasmids. As shown in this figure, the 293T cells infected with the VRPs expressed IKK protein.

Figure 14:
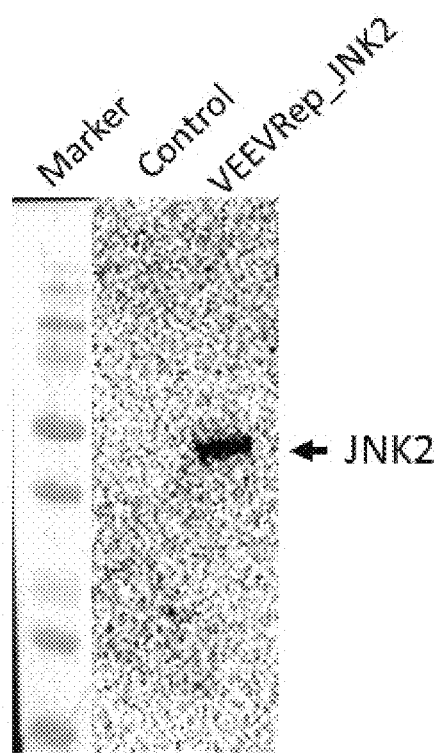
FIG. 14 shows western blotting of the cells infected by VRPs comprising a nucleotide encoding JNK2.

The expression of JNK2 from the replicon inserted JNK2 gene in the infected 293T cells was confirmed by western blotting. As the control, 293T cells without infection were used. Mouse anti-JNK2 antibody (Santa Cruz) was used as the first antibody (1:500) and HRP labelled anti-mouse IgG was used as the second antibody (1:4000). Results are shown in FIG. 14. 293T cells infected by the VRPs having JNK2 as the gene of interest were confirmed to express JNK2.

Example 6

Effect of Mutation in Capsid NLS

Two types of VRPs obtained in Example 4 using the following plasmids were used:
- i-1) plasmid comprising a polynucleotide encoding VEEV CT83 wild type capsid protein, or
- i-2) plasmid comprising a polynucleotide encoding VEEV CT83 capsid protein having a mutation in the NLS (K64N).
- ii) plasmid comprising a polynucleotide encoding wild type VEEV CT83 E3-E2-6K-E1, and
- iii) plasmid comprising polynucleotide encoding VEEV CT83 nsp1, nsp2, nsp3 and nsp4, and also a polynucleotide encoding luciferase.

Figure 15:
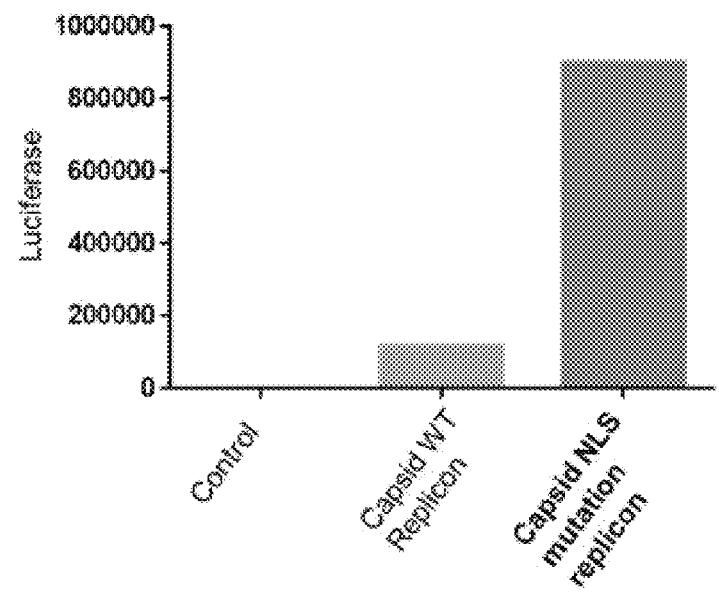
FIG. 15 shows the results of luciferase assay of the cells infected with VRPs comprising a gene encoding luciferase.

293T cells were infected with the VRPs in the same manner as Example 2. Luciferase assay was conducted in the same manner as Example 2. Results are shown in FIG. 15.

In this Figure, control correspond background of luciferase activity. VRPs with Capsid having mutation in NLS showed much higher luciferase activity (900556) compared to the VRPs with the WT capsid (118063).

The data indicated that modification of the capsid leads to higher yield and expression compared to the alphavirus replicon particle without modification in the capsid.

Example 7

Figure 16:
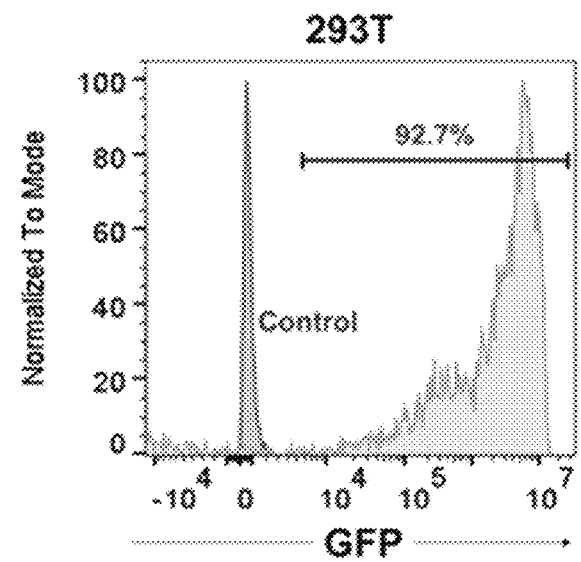
FIG. 16 shows the expression of GFP in the cells infected with VRPs comprising a gene encoding GFP.

VEE Virus replicon particles (VRPs) obtained in Example 4 by co-transfection of 293T cells with the following vectors were used:
- i) plasmid comprising a polynucleotide encoding VEEV CT83 capsid protein having a mutation in the NLS (K64N).
- ii) plasmid comprising a polynucleotide encoding wild type VEEV CT83 E3-E2-6K-E1.
- iii) plasmid comprising polynucleotide encoding VEEV CT83 nsp1, nsp2, nsp3 and nsp4, and a polynucleotide encoding GFP. 293T cells were infected with thus obtained VRPs in the same manner as Example 2. Control shows normal cells with no infection. The expression of GFP in the cells was confirmed. Results are shown in FIG. 16.

Example 8

The same VEEV replicon particles as those used in Example 7 were used. Macrophage J774. A1 cells and Bone Marrow-derived macrophage (BMDM) cells were infected with the VRPs. The gene of interest encoding GFP was expressed in the transfected macrophage cells.

Figure 17:
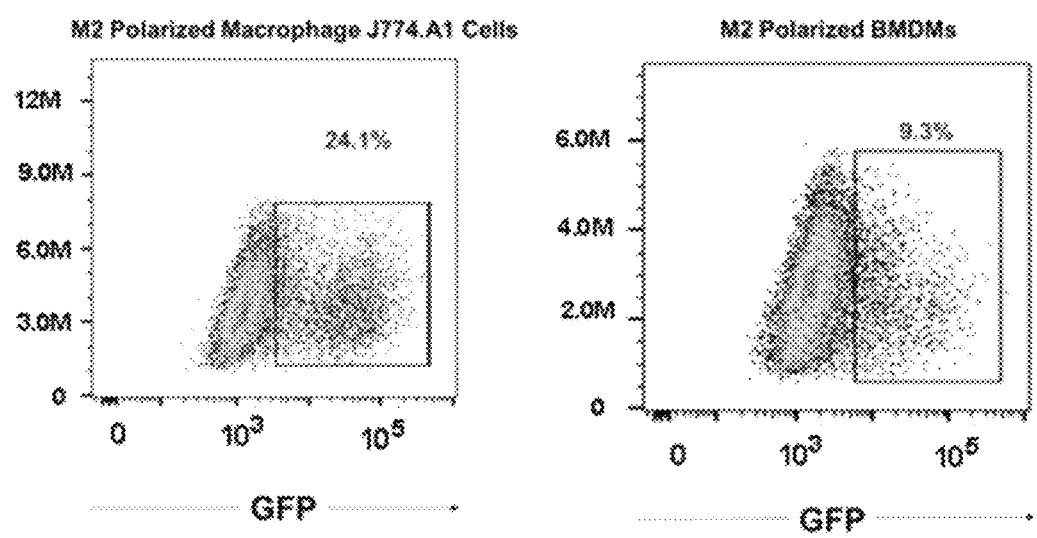
FIG. 17 shows the GFP expression in M2 polarized macrophage cells infected with VRPs comprising a gene encoding GFP.

The both cells were treated with IL-4 for 48 hours to be polarized and analyzed for GFP expression. Results are shown in FIG. 17.

Example 9

In Vivo Efficacy Study on CT26 Models

Figure 18:
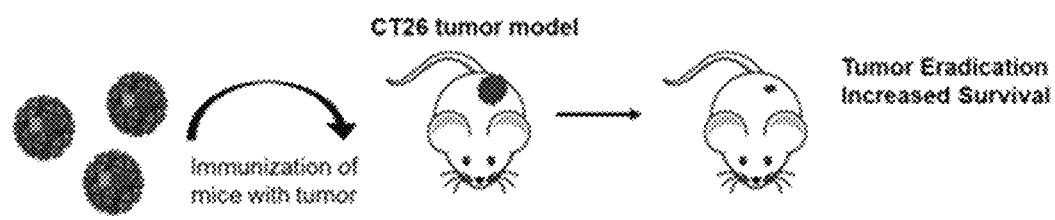
FIG. 18 shows schematic protocol of Example 9.

The schematic protocol of this example is shown in FIG. 18. VRPs used in this example were those prepared in Example 4 using the following plasmids:
- i) plasmid comprising a polynucleotide encoding VEEV CT83 capsid protein having a mutation in the NLS (K64N),
- ii) plasmid comprising a polynucleotide encoding wild type VEEV CT83 E3-E2-6K-E1, and
- iii) plasmid comprising polynucleotide encoding VEEV CT83 nsp1, nsp2, nsp3 and nsp4, and a polynucleotide encoding human IκB kinases (IKK).

This study consists of 4 arms, n=8, for a total of 32 animals. Animals were received Animals was randomized on Day 0 when tumor volume reaches 60-100 mm$^3$ and dosing will begin on Day 0 with G1: vehicle, G2: anti-PD-1 mAb, G3: VRPs and G4: a combination of VRPs and anti-PD-1 mAb at 10 mg/kg (BIWx3 and IP). The tumor growth was monitored until 30 days after the initiation of the treatment.

For groups 1, 3, 4, mice were intra-tumoraly injected with 50 μl of vehicle or VRPs dispersed in the vehicle on day 0, 2, 4, 6, 8 and 10. The VRPs or vehicle were administered into the tumor at the right flank using a 0.3 ml insulin type syringe. The aim was to use one entry point, but distribute the material through the tumor by moving the needle in and out.

Figure 19:
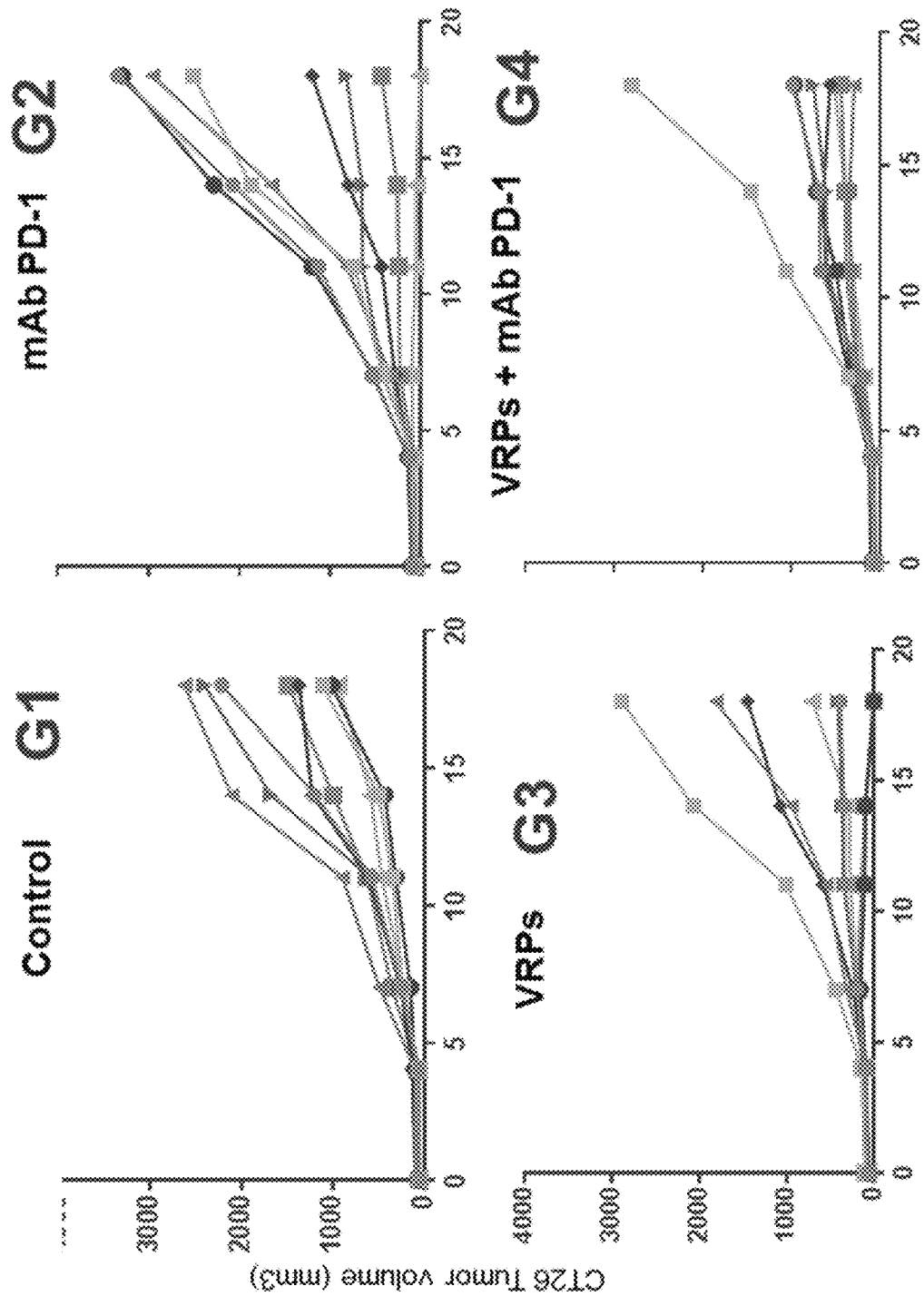
FIG. 19 shows the results of Example 9.

Measurements of tumor size were performed two times a week. The humane endpoint for this study is tumor burden of 3000 mm$^3$ and/or body weight loss of 20% or greater. The results of all 8 animals in each group are shown in FIG. 19.

The data indicated that VRPs comprising the gene encoding IKK and the combination of VRPs and anti-PD-1 antibody demonstrated superior anti-tumor effect over control and anti-PD-1 single immunotherapy.

Example 10

Chimeric Alphavirus replicon particles were prepared in the same manner as Example 4 using the following sets of vectors.

Chimeric ARP 1
- i) plasmid comprising a polynucleotide encoding wild type CHIKV 37997 strain capsid protein,
- ii) plasmid comprising a polynucleotide encoding wild type CHIKV 37997 strain E3-E2-6K-E1, and
- iii) plasmid comprising polynucleotide encoding VEEV CT83 nsp1, nsp2, nsp3 and nsp4, and a polynucleotide encoding GFP.

Chimeric ARP 2
- i) plasmid comprising a polynucleotide encoding wild type CHIKV OPY-1 strain capsid protein,
- ii) plasmid comprising a polynucleotide encoding wild type CHIKV OPY-1 strain E3-E2-6K-E1, and
- iii) plasmid comprising polynucleotide encoding VEEV CT83 nsp1, nsp2, nsp3 and nsp4, and a polynucleotide encoding GFP.

Figure 20:
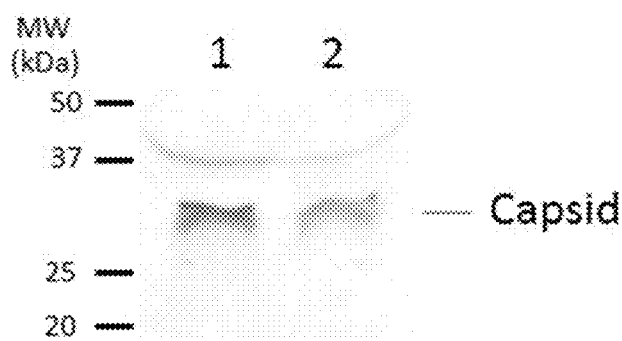
FIG. 20 shows western blotting of purified chimeric ARPs obtained from CHIKV structural proteins and VEEV replicon.

The obtained ARPs were purified in the same manner as Example 1. The purified chimeric ARPs were confirmed by western blotting using anti-CHIKV rabbit serum (1:2000) as the first antibody and goat anti-Rabbit IgG-HRP (1:4000) as the secondary antibody. The results are shown in FIG. 20. Generation of both chimeric ARPs were confirmed.

Figure 21:
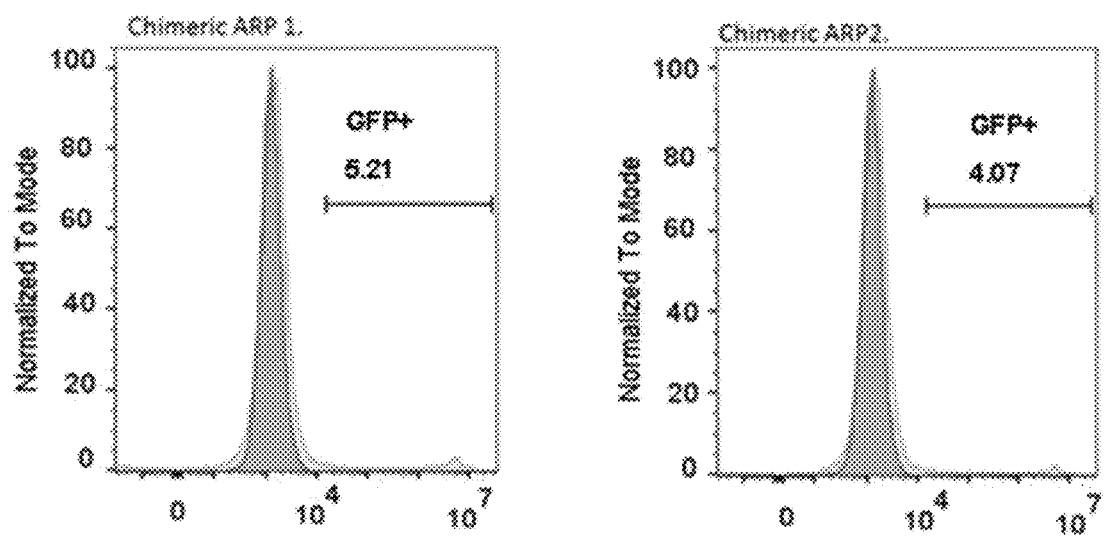
FIG. 21 shows FACS analysis of the cells infected by the ARPs of FIG. 20.

The 293T cells were infected with the chimeric ARPs encoding GFP. After the infection, cells were incubated for 48 hours and the expression of GEP was confirmed by FACS analysis. As a control, cells with no infection were used. Results are shown in FIG. 21. 5.21% and 4.07% of the cells infected with the ARPS expressed GFP, suggesting that the chimeric ARPs successfully expressed GFP protein (gene of interest is a nucleotide encoding GFP) in the cells.

What is claimed is:

1. A method for introducing a gene of interest into a cell in a subject in need thereof, which comprises administering to the subject an alphavirus replicon particle (ARP), which comprises
   (i) alphavirus structural proteins, wherein said alphavirus structural proteins comprise capsid protein, and E1 and E2 envelope proteins, and
   (ii) an alphavirus replicon comprising a polynucleotide encoding alphavirus nonstructural proteins nsp1, nsp2, nsp3 and nsp4 and at least one gene of interest,
   wherein said alphavirus capsid protein contains a mutation in the Nuclear Localization Signal (NLS), and wherein said mutation is the substitution of lysine with asparagine at the position corresponding to position 64 of VEEV virus capsid protein.

2. The method according to claim 1, wherein said E1 envelope protein comprises no amino acid alteration.

3. The method according to claim 1, wherein said alphavirus structural proteins are CHIKV structural proteins or VEEV structural proteins.

4. The method according to claim 1, wherein said alphavirus structural proteins are VEEV structural proteins.

5. The method according to claim 3, wherein said VEEV is VEEV strain TC-83.

6. The method according to claim 1, wherein said gene of interest encodes an antigen.

7. A method for introducing a gene of interest into a cell in a subject in need thereof, which comprises administering to the subject an alphavirus replicon particle (ARP), which comprises
   (i) CHIKV structural proteins, wherein said CHIKV structural proteins comprise capsid protein, and E1 and E2 envelope proteins, and
   (ii) an alphavirus replicon comprising a polynucleotide encoding alphavirus nonstructural proteins nsp1, nsp2, nsp3 and nsp4 and at least one gene of interest,
   wherein said alphavirus capsid protein contains a mutation in the Nuclear Localization Signal (NLS), and wherein said mutation is the substitution of lysine with asparagine at the position corresponding to position 64 of VEEV virus capsid protein.

8. The method of claim 7, wherein said E2 protein contains at least one substitution at a position selected from: the position corresponding to position 234 of CHIKV E2 protein; and the position corresponding to position 251 of CHIKV E2 protein.

9. The method of claim 7, wherein said CHIKV structural proteins further comprise envelope protein E3, and wherein said E3 protein contains an altered furin site resistant to furin cleavage.

10. The method according to claim 7, wherein said E1 envelope protein comprises no amino acid alteration.

11. The method of claim 7, wherein said CHIKV is CHIKV strain 37997 or strain OPY-1.

12. The method of claim 7, wherein said alphavirus nonstructural proteins are VEEV nonstructural proteins nsp1, nsp2, nsp2 and nsp4.

13. The method of claim 12, wherein said VEEV is VEEV strain TC-83.

14. The method of claim 7, wherein the gene of interest encodes an antigen.

* * * * *